US009035022B2

(12) United States Patent
Rivier

(10) Patent No.: US 9,035,022 B2
(45) Date of Patent: May 19, 2015

(54) CYCLIC CRF ANTAGONIST PEPTIDES

(75) Inventor: Jean E. F. Rivier, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 16 days.

(21) Appl. No.: 13/996,186

(22) PCT Filed: Dec. 22, 2011

(86) PCT No.: PCT/US2011/066787
§ 371 (c)(1),
(2), (4) Date: Oct. 2, 2013

(87) PCT Pub. No.: WO2012/088397
PCT Pub. Date: Jun. 28, 2012

(65) Prior Publication Data
US 2014/0024802 A1    Jan. 23, 2014

Related U.S. Application Data

(60) Provisional application No. 61/426,428, filed on Dec. 22, 2010.

(51) Int. Cl.
*A61K 38/00*     (2006.01)
*C07K 14/47*     (2006.01)
*C07K 14/575*    (2006.01)

(52) U.S. Cl.
CPC .................. *C07K 14/47* (2013.01); *A61K 38/00* (2013.01); *C07K 14/57509* (2013.01)

(58) Field of Classification Search
CPC ... A61K 38/00; C07K 14/47; C07K 14/57509
See application file for complete search history.

(56) References Cited

U.S. PATENT DOCUMENTS

| | | |
|---|---|---|
| 3,773,919 A | 11/1973 | Boswell et al. |
| 4,115,554 A | 9/1978 | Veber |
| 4,133,805 A | 1/1979 | Yardley |
| 4,140,767 A | 2/1979 | Veber |
| 4,161,521 A | 7/1979 | Veber et al. |
| 4,191,754 A | 3/1980 | Veber et al. |
| 4,238,481 A | 12/1980 | Rink et al. |
| 4,244,946 A | 1/1981 | Rivier et al. |
| 4,244,947 A | 1/1981 | Abraham et al. |
| 4,261,885 A | 4/1981 | Sakakibara et al. |
| 4,415,558 A | 11/1983 | Vale, Jr. et al. |
| 4,489,163 A | 12/1984 | Rivier et al. |
| 4,605,642 A | 8/1986 | Rivier et al. |
| 5,043,322 A | 8/1991 | Rivier et al. |
| 5,064,939 A | 11/1991 | Rivier et al. |
| 5,245,009 A | 9/1993 | Kornreich et al. |
| 5,278,146 A | 1/1994 | Rivier et al. |
| 5,493,006 A | 2/1996 | de Miranda et al. |
| 5,510,458 A | 4/1996 | Kornreich et al. |
| 5,663,292 A | 9/1997 | Rivier |
| 5,700,778 A | 12/1997 | Olivera et al. |
| 5,777,073 A | 7/1998 | Rivier |
| 5,807,986 A | 9/1998 | Rivier et al. |
| 5,824,771 A | 10/1998 | Rivier |
| 5,874,227 A | 2/1999 | Rivier |
| 5,925,730 A | 7/1999 | Semple et al. |
| 6,214,797 B1 | 4/2001 | Vale, Jr. et al. |
| 6,323,312 B1 | 11/2001 | Rivier |
| 6,326,463 B1 | 12/2001 | Rivier |
| 6,846,803 B1 | 1/2005 | Spiess et al. |
| 7,141,546 B1 | 11/2006 | Rivier et al. |
| 7,498,300 B2 | 3/2009 | Rivier et al. |
| 7,815,905 B2 | 10/2010 | Chen et al. |
| 2014/0088105 A1 | 3/2014 | Beattie et al. |

FOREIGN PATENT DOCUMENTS

| | | |
|---|---|---|
| WO | WO 96/19499 A2 | 6/1996 |
| WO | WO 2007/149938 A2 | 12/2007 |
| WO | WO 2012/088397 A2 | 6/2012 |

OTHER PUBLICATIONS

Beyermann et al., "A Single-Point Slight Alteration Set as a Tool for Structure-Activity Relationship Studies of Ovine Corticotropin Releasing Factor," *J Med Chem*. 39:3324-3330, 1996.
Farrokhi et al., "Cortagine: Behavioral and Autonomic Function of the Selective CRF Receptor Subtype 1 Agonist," *CNS Drug Rev*. 13:423-443, 2007.
Grace et al., "Common and Divergent Structural Features of a Series of Corticotropin Releasing Factor-Related Peptides," *J Am Chem Soc*. 129:16102-16114, 2007.
International Search Report dated Jul. 13, 2012 for PCT/US2011/066787.
Larauche et al., "Cortagine, a CFR1 Agonist, Induces Stresslike Alternations of Colonic Function and Visceral Hypersensitivity in Rodents Primarily Through Peripheral Pathways," *Am J Physiol Gastrointest Liver Physiol*. 297:G215-G227, 2009.
Rivier et al., "Constrained Corticotropin Releasing Factor Antagonists (Astressin Analogues) with Long Duration of Action in the Rat," *J Med Chem*. 42:3175-3182, 1999.
Rivier et al., "Potent and Long-Acting Corticotropin Releasing Factor (CRF) Receptor 2 Selective Peptide Competitive Antagonists," *J Med Chem*. 45:4737-4747, 2002.
Rivier et al., "Stressin1-A, a Potent Corticotropin Releasing Factor Receptor 1 (CRF1)-Selective Peptide Agonist," *J Med Chem*. 50:1668-1674, 2007.
Extended European Examination Report for EP 11851321.6 dated Jul. 15, 2014 (16 pages).
Tezval et al., "Cortagine, a Specific Agonist of Corticotropin-Releasing Factor Receptor Subtype 1, is Anxiogenic and Antidepressive in the Mouse Model," *Proc Nall Acad Sci. USA* 101:9468-9473, 2004.
Zorrilla and Koob, "Progress in Corticotropin-Releasing Factor-1 Antagonist Development," *Drug Discov Today* 15:371-383, 2010.

*Primary Examiner* — Thomas S Heard
(74) *Attorney, Agent, or Firm* — Klarquist Sparkman, LLP

(57) ABSTRACT

Cyclic CRF antagonist peptides having improved properties of "drugability". The peptides are 33 residues in length with a lactam bond between the residues in position 22 and 25; however, they may be N-terminally shortened by up to 3 residues.

27 Claims, No Drawings

CYCLIC CRF ANTAGONIST PEPTIDES

CROSS-REFERENCE TO RELATED APPLICATIONS

This application is the national stage of PCT/US2011/66787 filed Dec. 22, 2011, which claims priority from U.S. Provisional Application No.: 61/426,428 filed Dec. 22, 2010, the disclosure of which is incorporated herein by reference.

GOVERNMENT SUPPORT

This invention was made with Government support under grant number P01-DK-26741 awarded by the National Institutes of Health. The Government has certain rights in this invention.

FIELD

This invention is generally directed to peptides and to the pharmaceutical treatment of mammals using such peptides. More specifically, the invention relates to cyclic antagonists of the CRF hentetracontapeptides as well as to members of the larger family of CRF-like peptides, to pharmaceutical compositions containing such cyclic CRF antagonists, to methods of treatment of mammals using such cyclic CRF antagonists, and to methods of screening for new drugs using such peptides.

BACKGROUND OF THE INVENTION

Experimental and clinical observations have supported the concept that the hypothalamus plays a key role in the regulation of adenohypophysial corticotropic cells' secretory functions. Over 50 years ago it was demonstrated that factors present in the hypothalamus would increase the rate of ACTH secretion by the pituitary gland when incubated in vitro or maintained in an organ culture. However, a physiologic corticotropin releasing factor (CRF) was not characterized until ovine CRF (oCRF) was characterized in 1981. As disclosed in U.S. Pat. No. 4,415,558, the disclosure of which is incorporated herein by reference, oCRF was found to be a 41-residue amidated peptide. oCRF lowers blood pressure in mammals when injected peripherally and stimulates the secretion of ACTH and β-endorphin.

Rat CRF (rCRF) was later isolated, purified and characterized; it was found to be a homologous, amidated hentetracontapeptide as described in U.S. Pat. No. 4,489,163, the disclosure of which is also incorporated herein by reference. The amino acid sequence of human CRF was later determined to be the same as that of rCRF. rCRF and hCRF are used interchangeably to describe this peptide, and the designation r/hCRF is frequently used with respect to this peptide hormone. These peptide hormones are considered to form a part of a larger family of native CRF-like peptides and analogs which include the mammalian and fish CRFs, the urotensins and sauvagine, as discussed in Vale et al., "Characterization of the Hypothalamic Peptide: Corticotropin Releasing Factor", *Proceedings of the Naito International Symposium on Natural and Biological Activity*, Tokyo, Japan, Nov. 5-7, 1985, and Lederis et al., "Neurohormones from Fish Tails, II: Actions of Urotensin I in Mammals and Fishes", *Recent Progress in Hormone Research*, Vol. 41, Academic Press, Inc. (1985).

Although originally isolated and characterized on the basis of its role in this hypothalamo-pituitary- adrenal (HPA) axis, CRF has been found to be distributed broadly throughout the central nervous system as well as in extraneural tissues, such as the adrenal glands, placenta and testes, where it may also act as a paracrine regulator or a neurotransmitter. Moreover, the involvement of CRF in affective disorders, such as anxiety, depression, alcoholism and anorexia nervosa, and in modulating reproduction and immune responses suggests that changes in CRF expression may have important physiological and pathophysiological consequences. For example, perturbations in the regulatory loops comprising the HPA axis often produce chronically elevated levels of circulating glucocorticoids; such patients display the physical hallmarks of Cushing's syndrome, including truncal obesity, muscle-wasting, and reduced fertility.

In addition to its role in mediating activation of the HPA axis, CRF has also been shown to modulate autonomic and behavioral changes, some of which occur during the stress response. Many of these behavioral changes have been shown to occur independently of HPA activation in that they are not duplicated by dexamethasone treatment and are insensitive to hypophysectomy. In addition, direct infusion of CRF into the CNS mimics autonomic and behavioral responses to a variety of stressors. Because peripheral administration of CRF or a CRF antagonist fails to affect certain of these changes, it appears that CRF exhibits a direct brain action with respect to such functions, which include appetite suppression, increased arousal and learning ability. However, CRF antagonists given peripherally block endogenous CRF-mediated increases in ACTH secretion, and when such are delivered into the cerebral ventricles, stress-induced changes in autonomic activity and behavior can be mitigated.

As a result of the extensive anatomical distribution and multiple biological actions of CRF, this regulatory peptide is now believed to be involved in the regulation of numerous biological processes. CRF has also been implicated in the regulation of inflammatory responses. Although it has been observed that CRF plays a pro-inflammatory role in certain animal models, CRF appears to suppress inflammation in other models by reducing injury-induced increases in vascular permeability.

CRF analogs containing D-isomers of certain a-amino acids have been developed, such as those shown in U.S. Pat. No. 5,278,146. Synthetic r/hCRF and oCRF stimulate ACTH and β-endorphin-like activities (β-END-Li) in vitro and in vivo, and they substantially lower blood pressure when injected peripherally. Antagonists of these peptides and of sauvagine and urotensin are disclosed in U.S. Pat. No. 4,605,642, issued Aug. 12, 1986, the disclosure of which is incorporated herein by reference. Additional biopotent CRF antagonists have been developed, and are disclosed in U.S. Pat. Nos. 5,245,009; 5,493,006; 5,510,458; 5,663,292; 5,777,073; 5,874,227; and 6,323,312.

CRF antagonist peptides have been developed during the last 10-15 years which exhibit longer lasting and increased biological activity, in comparison to previously known CRF antagonists, and little or substantially no residual CRF agonist activity. Many of these exhibit high receptor affinity.

It has been shown that various of the members of the family of CRF-like peptides can be modified to create highly biopotent CRF antagonists that bind strongly to the known CRF receptors (CRF-R), including CRFR1 and CRFR2, without significantly activating such receptors and thus block the action of endogenous CRF at its receptors. They exhibit an affinity for CRFR1 and CRFR2 higher than that exhibited by oCRF. These modifications to create such bioactive CRF antagonists have included N-terminally shortening the native or other molecule so that it has a length of 30 to 33 residues, e.g. r/hCRF(9-41), r/hCRF(10-41), r/hCRF(11-41) and r/hCRF(12-41), and incorporating a cyclizing bond, preferably a lactam, which joins the side chains of the residues that are located in the positions of the 8th and 11th residues from the C-terminal residue, e.g. (cyclo 30-33)[Glu$^{30}$, Lys$^{33}$]r/hCRF(12-41). It was found that such a cyclizing modification often very substantially increased the biopotency of the comparable linear peptide. It was also found that the combination of this cyclizing bond plus the acylation of the N-terminus created a molecule of long-acting duration and that such an effect may be greatest in a peptide of 33 residues in length, e.g. (cyclo 30-33)[Ac-Asp$^9$, Glu$^{30}$, Lys$^{33}$]-r/hCRF(9-41). The family of CRF-like peptides is generally considered to encompass those peptides which bind to the CRF receptors and have at least about 45% amino acid structural homology with ovine CRF, the first mammalian CRF isolated and characterized. The CRF-like family includes, but is not limited to, the following known peptides: ovine CRF, rat/human CRF, porcine CRF, bovine CRF, fish CRFs, carp urotensin, sucker urotensin, maggy sole urotensin, flounder urotensin, sauvagine, the urocortins 1, 2 and 3, and stresscopins.

Efforts for improving CRF antagonists have generally concentrated on increasing affinity for one or the other known receptors (CRFR1 and CRFR2) or for both receptors (CRFR1/2) with just one antagonist. Scant effort has been expended at optimizing the physical/chemical properties towards obtaining clinically safe, potent, stable, inexpensive-to-make analogs, i.e., improving "drugability" of such analogs. The search for CRF antagonists having ever-improved drugability continues.

SUMMARY OF THE INVENTION

One class of CRF antagonist peptides has now been identified which is defined by the following general formula: A-D-Xaa-B-Xaa$_c$-Xaa$_a$-Xaa$_b$-Xaa$_b$-C—NH$_2$ wherein A is Asp-Leu-Thr or Asp-Leu-Ser or an N-terminally shortened version thereof; D-Xaa is D-Phe, D-2Nal, D-Leu, D-Tyr, D-Cpa, D-pNO$_2$Phe, or D-Aph(Cbm); B is a sequence of 17 amino acid residues that is found between Phe in the 12-position and Gln in position-30 of r/hCRF or the corresponding sequence of another peptide of the CRF-like family as described above; Xaa$_c$ represent a pair of amino acid residues, the side chains of which are linked in a lactam bridge cyclizing bond; Xaa$_a$ is a natural α-amino acid residue other than Cys; Xaa$_b$ is CML, D-CML, CMV, CMP, D-Aph(Cbm) or D-Aph(Hor); and C is a sequence of the last 8 amino acid residues of the C-terminal portion of a peptide of the CRF family. The N-terminus of the peptide is N-acylated. Additional substitutions such as are presently well known in the field of CRF antagonists may also be made in these modified cyclic peptides, e.g. the substitution of Met by Nle or Leu. Moreover, the N-terminus may be shortened by deleting Asp or Asp-Leu or all of A (i.e. des A) to provide peptides that continue to exhibit CRF antagonist characteristics.

As indicated above, these peptides have a cyclizing bond between the residues in what would be the 30- and 33-positions in mammalian CRF. This bond is preferably an amide bond (or lactam bridge) between side chain carboxyl and amino groups. Most preferably, there is a lactam bridge between a side chain carboxyl group on the residue in the 30-position, preferably Glu or Asp, and a side chain amino group on the 33-position residue, preferably Lys or Orn or alternatively Dbu, Dpr, or Hly. Except for the fact that CRF agonists are being used clinically for diagnostic purposes of the HPA axis, native CRFs, such as ovine CRF, r/hCRF, sauvagine, urotensins, urocortins I, II and III and stresscopins, are not considered to have drug-like properties in terms of safety, chemical and biological stability leading to long duration of action.

These peptides also have the preferred inclusion of D-Phe, D-2Nal or D-Leu or an equivalent D-isomer, e.g., D-pNO$_2$Phe, D-Cpa, D-Tyr, D-Trp or D-3Pal, in what would be the 12-position of r/hCRF. They preferably have norleucine (Nle) substituted for any naturally occurring Met, e.g., in what would be the 21 and 38 positions of r/hCRF. If it is desired to label the peptide as by adding a radioactive isotope or a fluorescent dye as is well known in this art, D-Tyr, Tyr or an acyl group having a hydroxy aryl moiety (e.g. des-NH$_2$-Tyr) may be added at the N-terminus; Ac-D-Tyr or Ac-Tyr may also be used. When the N-terminus is to be radioiodinated, it may be preferable to substitute Arg for Lys in what would be the 36-position of CRF as it is generally considered to be structural equivalent which may be more stable. Other optional substitutions may also be made throughout the molecule as previously taught, and these are considered to be functional equivalents of the specific peptides described hereinafter. For example, it was found that analogs wherein one of more Leu residues are substituted with a methyl group on the a-carbon atom, i.e., CML, the analog may exhibit certain improved properties. Again, with respect to the AA sequence of r/hCRF, CML may optionally be present in the 10-, 14-, 15-, 17-, 18-, 24-, 27-, 36-, 37-, 38-, 40- and/or 41-positions, and similarly, α-aminoisobutyric acid (Aib) or dipropylglycine (Dpg) may be optionally inserted at one or more of positions 22, 24, 28, 29, 31, 32, 34, 39, 40 and 41. Such substitutions may often enhance biopotency and/or to increase duration of action and have not been found to have any undesirable effect.

As earlier indicated, these improved CRF antagonists are created by shortening the N-terminus of a native CRF-like peptide or analog thereof and incorporating the desired substitutions. Preferably, a sequence of 8 or 9 residues beginning at the N-terminus of the native molecule is deleted; however, 10 or 11 may be deleted. For example, when a mammalian CRF is shortened, the resultant molecule may be accordingly referred to as CRF(9-41), CRF(10-41), CRF(11-41) or CRF (12-41), depending upon the number of residues deleted; the longer analogs CRF(9-41) and CRF(10-41) with an acylated N-terminus are preferred for peptides that will exhibit long duration of biopotency.

Pursuant to the teachings of U.S. Pat. No. 5,874,227, a CRF antagonist showing favorable characteristics was developed, and it has undergone some significant testing. It is now often referred to by the shorthand name Astressin; it is a 30-residue cyclic peptide having the formula: cyclo(30-33)[D-Phe$^{12}$, Nle$^{21,38}$,Glu$^{30}$,Lys$^{33}$]-h/rCRF(12-41). Its amino-acid sequence is:

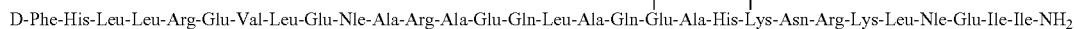

D-Phe-His-Leu-Leu-Arg-Glu-Val-Leu-Glu-Nle-Ala-Arg-Ala-Glu-Gln-Leu-Ala-Gln-Glu-Ala-His-Lys-Asn-Arg-Lys-Leu-Nle-Glu-Ile-Ile-NH$_2$.

CRF antagonists have now been developed that have improved drugability when compared to Astressin and to other CRF antagonists developed by our laboratory. These are hereinafter referred to with shorthand names based upon the antagonist Astressin B, rather than upon the agonist r/hCRF. Astressin B is a modified version of Astressin that is extended by the residues Asp-Leu-Thr at the N-terminus and substituted by CML at positions 27 and 40, which are positions 19 and 32 of the 33-residue peptide.

Certain of these improved CRF antagonists will form fibrils upon injection and thus exhibit Depot Formulation. Others exhibit particularly advantageous solubility properties whereas others exhibit biological potency of long duration. In other words, such desirable CRF antagonists or their salts that are less soluble than Astressin in aqueous buffers will have greater solubility in oils and vice versa.

Pharmaceutical compositions in accordance with the invention include such CRF antagonists or nontoxic addition salts thereof that are dispersed in a pharmaceutically acceptable liquid or solid carrier. Such drug formulations are facilitated because these particular analogs exhibit higher or lower solubility at physiological pH than Astressin B. For subcutaneous (s.c.) administration, formulations in aqueous solutions of mannitol, corn oil, or peanut oil may be preferred wherein such high solubility remains.

The administration of such peptides or pharmaceutically acceptable addition salts thereof to mammals, particularly humans, in accordance with the invention may be carried out for the regulation of secretion of ACTH, β-endorphin, β-lipotropin, corticosterone and other products of the pro-opiomelanocortin (POMC) gene and/or for affecting mood, behavioral and gastrointestinal functions and autonomic nervous system activities. For example, these CRF antagonists may be administered to reduce high ACTH levels, and thereby treat stress-related illnesses, such as stress-induced immune responses that affect hair loss, the gastrointestinal tract, i.e. particularly to treat patients suffering from irritable bowel syndrome and gastrointestinal diseases, and also to treat inflammatory disorders; immune suppression; human immunodeficiency virus (HIV) infections; Alzheimer's disease; anorexia nervosa; hemorrhagic stress; drug and alcohol withdrawal symptoms; drug addiction, psoriasis, rheumatoid arthritis and infertility. Because of these broad effects, it may be desirable to administer these peptides with hormonal replacement therapy as discussed hereinafter.

These peptides may also provide the basis for valuable methods for drug-screening; such may detect even more potent molecules that will bind to and/or activate CRF receptors as a result of their high affinity for CRF receptors.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations are used to identify the alpha-amino acid residues, and where the amino acid residue has isomeric forms, it is the L-form of the amino acid that is represented unless otherwise expressly indicated, e.g. Ser=L-serine, Orn=L-ornithine, Nle=L-norleucine, Nva=L-norvaline, Agl=aminoglycine, Dbu=L-2,4-diaminobutyric acid, Dpr=L-2,3-diaminopropionic acid, Hly=L-homolysine and Har=L-homoarginine. In addition the following abbreviations are used: CML=$C^{\alpha}CH_3$-L-leucine; CMP=$C^{\alpha}CH_3$-L-phenylalanine; CMV=$C^{\alpha}CH_3$-L-valine; Aib=2-aminoisobutyric acid; Dpg=dipropylglycine; Nal=L-β-(1- or 2-naphthyl)alanine; Pal=L-β-(2-,3- or 4-pyridyl)alanine; Cpa=L-(2-, 3-, or 4-chloro) phenylalanine; Aph=L-(2-, 3- or 4-amino)phenylalanine; Amp=(2-, 3- or 4-aminomethyl)phenylalanine; Hor=L-hydroorotyl; Nic=3-carboxypyridine (or nicotinic acid); Cbm=carbamoyl; Acr=acrylyl; Pn=propionyl; iPn=isopropionyl; Bt=butyryl; Vl=valeryl; Vac=vinylacetyl; Nph=naphthoyl; and Flu=fluorenoyl.

These CRF antagonists include a D-isomer in what would be the 12-position of r/hCRF and would be the 4-position of Astressin B (which can be at the N-terminus, although the peptide is preferably extended). The cyclic peptides have the following formula, or are equivalent nontoxic salts thereof:

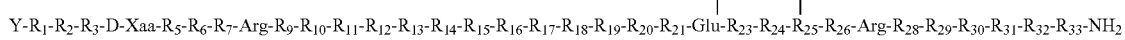

Y-$R_1$-$R_2$-$R_3$-D-Xaa-$R_5$-$R_6$-$R_7$-Arg-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-Glu-$R_{23}$-$R_{24}$-$R_{25}$-$R_{26}$-Arg-$R_{28}$-$R_{29}$-$R_{30}$-$R_{31}$-$R_{32}$-$R_{33}$-$NH_2$ wherein Y is H, Tyr or D-Tyr or an acyl group having up to 15 to 20 carbon atoms, preferably up to 12 carbon atoms, and more preferably 1 to 7 carbon atoms, e.g. Ac, For, Acr or Bz; $R_1$ is Asp or des-$R_1$; $R_2$ is Leu or des-$R_2$; $R_3$ is Ser or Thr or des-$R_3$; D-Xaa is D-Phe, D-Leu, D-Tyr, D-Cpa, D-pNO$_2$Phe, D-Nal, D-Trp, D-Aph(Cbm) or D-Pal; $R_5$ is His, Tyr or Glu; $R_6$ is CML or Leu; $R_7$ is Leu or CML; $R_9$ is Glu, CML, Asn or Lys; $R_{10}$ is Val, CML, Nle or Met; $R_{11}$ is Leu, CML or Ile; $R_{12}$ is Glu, D-Glu or His; $R_{13}$ is Nle, Leu, Nva or Met; $R_{14}$ is Ala, D-Ala, Aib, Dpg, Thr, D-Thr, Glu or D-Glu; $R_{15}$ is Arg, Orn or Lys; $R_{16}$ is Ala, Aib, Dpg or CML; $R_{17}$ is Glu or Asp; $R_{18}$ is Gln, Asn or Lys; $R_{19}$ is Leu, CML, Aib, Dpg, CMP or CMV; $R_{20}$ is Ala, Dpg, or Aib; $R_{21}$ is Gln, Aib, Dpg or Glu; $R_{23}$ is Ala, Dpg or Aib; $R_{24}$ is Aib, Dpg, CML, D-CML, D-Aph (Cbm) or D-Aph(Hor); $R_{25}$ is Lys or Orn; $R_{26}$ is Asn, Aib, Dpg, CML or D-CML; $R_{28}$ is Lys, Orn, Arg, Har, CML or Leu; $R_{29}$ is CML, Leu or Tyr; $R_{30}$ is Nle, CML or Met; $R_{31}$ is Glu, Aib, Dpg or Asp; $R_{32}$ is CMP, CMV, CML, Ile, Aib, Dpg, Thr, Asn, Glu, Ala, Val, Leu, Nle, Phe, Nva, Gly or Gln; and $R_{33}$ is Ala, Aib, Dpg, Ile, Gly, Val, Leu, CML, Nle, Phe, Nva or Gln; provided that $R^{19}$ is Aib, Dpg, CMP or CMV or that $R^{24}$ is CML, D-CML, CMV, CMP, D-Aph(Cbm) or D-Aph (Hor). As an alternative to such optional acylation at the N-terminus, a sulfonamide may be formed, or a sugar or a lipid can be added to modulate hydrophilicity and therefore duration of action and solubility. By des-$R_1$ is meant that the residue which would be in that position is deleted.

Still another group of preferred CRF antagonists has the following formula (including nontoxic salts thereof):

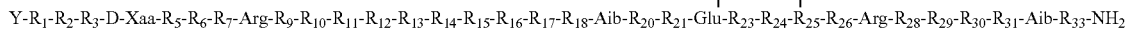

Y-$R_1$-$R_2$-$R_3$-D-Xaa-$R_5$-$R_6$-$R_7$-Arg-$R_9$-$R_{10}$-$R_{11}$-$R_{12}$-$R_{13}$-$R_{14}$-$R_{15}$-$R_{16}$-$R_{17}$-$R_{18}$-Aib-$R_{20}$-$R_{21}$-Glu-$R_{23}$-$R_{24}$-$R_{25}$-$R_{26}$-Arg-$R_{28}$-$R_{29}$-$R_{30}$-$R_{31}$-Aib-$R_{33}$-$NH_2$ wherein Y is H, Tyr or D-Tyr or an acyl group having up to 15 carbon atoms, preferably up to 12 carbon atoms, and more preferably 1 to 7 carbon atoms, e.g. Ac, For, Acr or Bz; $R_1$ is Asp or des-$R_1$; $R_2$ is Leu or des-$R_2$; $R_3$ is Ser or Thr or des-$R_3$; D-Xaa is D-Phe, D-Leu, D-Tyr, D-Cpa, D-Nal, D-Trp or D-Pal; $R_5$ is His, Tyr or Glu; $R_6$ is CML or Leu; $R_7$ is Leu or CML; $R_9$ is Glu, CML, Asn or Lys; $R_{10}$ is Val, CML, Nle or Met; $R_{11}$ is Leu, CML or Ile; $R_{12}$ is Glu, D-Glu or His; $R_{13}$ is Nle or Met; $R_{14}$ is Ala, D-Ala, Aib, Thr, D-Thr, Glu or D-Glu; $R_{15}$ is Arg, Orn or Lys; $R_{16}$ is Ala, Aib or CML; $R_{17}$ is Glu or Asp; $R_{18}$ is Gln, Asn or Lys; $R_{20}$ is Ala or Aib; $R_{21}$ is Gln, Aib or Glu; $R_{23}$ is Ala or Aib; $R_{24}$ is His, Aib, D-Aph(Cbm) or CML; $R_{25}$ is Lys or Orn; $R_{26}$ is Asn or Aib; $R_{28}$ is Lys, Orn, Arg, Har, CML or Leu; $R_{29}$ is CML, Leu or Tyr; $R_{30}$ is Nle, CML or Met; $R_{31}$ is Glu, Aib or Asp; and $R_{33}$ is Ala, Aib, Ile, Gly, Val, Leu, CML, Nle, Phe, Nva or Gln.

Another preferred group of CRF antagonists has the following formula (including nontoxic salts thereof):

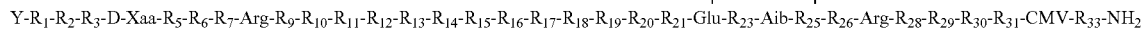

wherein Y is H, Tyr or D-Tyr or an acyl group having up to 15 carbon atoms, preferably up to 12 carbon atoms, and more preferably 1 to 7 carbon atoms, e.g. Ac, For, Acr or Bz; $R_1$ is Asp or des-$R_1$; $R_2$ is Leu or des-$R_2$; $R_3$ is Ser or Thr or des-$R_3$; D-Xaa is D-Phe, D-Leu, D-Tyr, D-Cpa, D-Nal, D-Trp or D-Pal; $R_5$ is His, Tyr or Glu; $R_6$ is CML or Leu; $R_7$ is Leu or CML; $R_9$ is Glu, CML, Asn or Lys; $R_{10}$ is Val, CML, Nle or Met; $R_{11}$ is Leu, CML or Ile; $R_{12}$ is Glu, D-Glu or His; $R_{13}$ is Nle or Met; $R_{14}$ is Ala, D-Ala, Aib, Thr, D-Thr, Glu or D-Glu; $R_{15}$ is Arg, Orn or Lys; $R_{16}$ is Ala, Aib or CML; $R_{17}$ is Glu or Asp; $R_{18}$ is Gln, Asn or Lys; $R_{19}$ is CMV or Aib; $R_{20}$ is Ala or Aib; $R_{21}$ is Gln, Aib or Glu; $R_{23}$ is Ala or Aib; $R_{25}$ is Lys or Orn; $R_{26}$ is Asn or Aib; $R_{28}$ is Lys, Orn, Arg, Har, CML or Leu; $R_{29}$ is CML, Leu or Tyr; $R_{30}$ is Nle, CML or Met; $R_{31}$ is Glu, Aib or Asp; and $R_{33}$ is Ala, Aib, Ile, Gly, Val, Leu, CML, Nle, Phe, Nva or Gln. When it is desired that the peptide very closely resemble r/hCRF, all or a majority of the following selections are incorporated: $R_{10}$ is Val, $R_{14}$ is Ala, $R_{15}$ is Arg, $R_{16}$ is Ala, $R_{17}$ is Glu, $R_{20}$ is Ala, $R_{31}$ is Glu, and $R_{33}$ is Ile.

Yet another preferred group of antagonists is based upon the sequences of r/hCRF and oCRF and because of the syntheses that have been carried out over the last decade, it has uniformly been shown that any of the residues in the corresponding position in ovine CRF can be substituted into the amino acid sequence of r/hCRF without significantly altering its biopotency. This group has the following formula (including nontoxic salts thereof):

wherein Y is H, Tyr or D-Tyr or an acyl group having up to 15 carbon atoms, preferably up to 12 carbon atoms, and more preferably 1 to 7 carbon atoms, e.g. Ac, For, Acr or Bz; $R_1$ is Asp or des-$R_1$; $R_2$ is Leu or des-$R_2$; $R_3$ is Ser or Thr or des-$R_3$; D-Xaa is D-Phe, D-Leu, D-Tyr, D-Cpa, D-Nal, D-Trp or D-Pal; $R_5$ is His, Tyr or Glu; $R_6$ is CML or Leu; $R_7$ is Leu or CML; $R_9$ is Glu, CML, Asn or Lys; $R_{10}$ is Val, CML, Nle or Met; $R_{11}$ is Leu, CML or Ile; $R_{12}$ is Glu, D-Glu or His; $R_{13}$ is Nle or Met; $R_{14}$ is Ala, D-Ala, Aib, Thr, D-Thr, Glu or D-Glu; $R_{15}$ is Arg, Orn or Lys; $R_{16}$ is Ala, Aib or CML; $R_{17}$ is Glu or Asp; $R_{18}$ is Gln, Asn or Lys; $R_{20}$ is Ala or Aib; $R_{21}$ is Gln, Aib or Glu; $R_{23}$ is Ala or Aib; $R_{25}$ is Lys or Orn; $R_{26}$ is Asn or Aib; $R_{28}$ is Lys, Orn, Arg, Har, CML or Leu; $R_{29}$ is Tyr; $R_{30}$ is Nle, CML or Met; $R_{31}$ is Glu, Aib or Asp; and $R_{33}$ is Ala, Aib, Ile, Gly, Val, Leu, CML, Nle, Phe, Nva or Gln.

A further group of CRF antagonists has the formula (including nontoxic salts thereof):

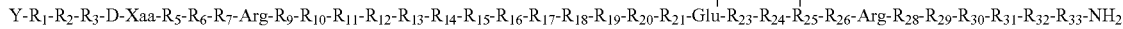

wherein Y is H, Tyr or D-Tyr or an acyl group having up to 15 carbon atoms, preferably up to 12 carbon atoms, and more preferably 1 to 7 carbon atoms, e.g. Ac, For, Acr or Bz; $R_1$ is Asp or des-$R_1$; $R_2$ is Leu or des-$R_2$; $R_3$ is Ser or Thr or des-$R_3$; D-Xaa is D-Phe, D-Leu, D-Tyr, D-Cpa, D-Nal, D-Trp or D-Pal; $R_5$ is His, Tyr or Glu; $R_6$ is CML or Leu; $R_7$ is Leu or CML; $R_9$ is Glu, CML, Asn or Lys; $R_{10}$ is Val, CML, Nle or Met; $R_{11}$ is Leu, CML or Ile; $R_{12}$ is Glu, D-Glu or His; $R_{13}$ is Nle or Met; $R_{14}$ is Ala, D-Ala, Aib, Thr, D-Thr, Glu or D-Glu; $R_{15}$ is Arg, Orn or Lys; $R_{16}$ is Ala, Aib or CML; $R_{17}$ is Glu or Asp; $R_{18}$ is Gln, Asn or Lys; $R_{19}$ is Leu or CML; $R_{20}$ is Ala or Aib; $R_{21}$ is Gln, Aib or Glu; $R_{23}$ is Ala or Aib; $R_{24}$ is D-Aph (Cbm), CML, D-CML or D-Aph(Hor); $R_{25}$ is Lys or Orn; $R_{26}$ is Asn or Aib; $R_{28}$ is Lys, Orn, Arg, Har, CML or Leu; $R_{29}$ is CML, Leu or Tyr; $R_{30}$ is Nle, CML or Met; $R_{31}$ is Glu, Aib or Asp; $R_{32}$ is CML, Ile, Aib, Thr, Asn, Glu, Ala, Val, Leu, Nle, Phe, Nva, Gly or Gln; and $R_{33}$ is Ala, Aib, Ile, Gly, Val, Leu, CML, Nle, Phe, Nva or Gln. Specific analogs of this group which are considered to be particularly biopotent from the standpoint of reducing high ACTH and cortisol levels are:
[D-Aph(Cbm)$^{24}$]-Astressin B;
[CML$^{24}$]-Astressin B;
[D-CML$^{24}$]-Astressin B; and
[D-Aph(Hor)$^{24}$]-Astressin B.

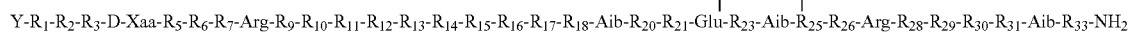

When Tyr or D-Tyr is present at the N-terminus, the peptide can be conveniently radiolabelled using $^{125}$I.

A still further preferred group of CRF antagonists has the formula (including nontoxic salts thereof):

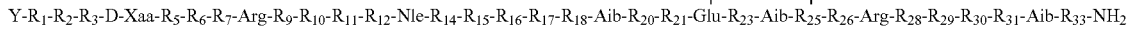

Y-$R_1$-$R_2$-$R_3$-D-Xaa-$R_5$-$R_6$-$R_7$-Arg-$R_9$-$R_{10}$-$R_{11}$-$R_{12}$-Nle-$R_{14}$-$R_{15}$-$R_{16}$-$R_{17}$-$R_{18}$-Aib-$R_{20}$-$R_{21}$-Glu-$R_{23}$-Aib-$R_{25}$-$R_{26}$-Arg-$R_{28}$-$R_{29}$-$R_{30}$-$R_{31}$-Aib-$R_{33}$-$NH_2$ wherein Y is H, Tyr or D-Tyr or an acyl group having up to 15 carbon atoms, preferably up to 12 carbon atoms, and more preferably 1 to 7 carbon atoms, e.g. Ac, For, Acr or Bz; $R_1$ is Asp or des-$R_1$; $R_2$ is Leu or des-$R_2$; $R_3$ is Ser or Thr or des-$R_3$; D-Xaa is D-Phe, D-Leu, D-Tyr, D-Cpa, D-Nal, D-Trp or D-Pal; $R_5$ is His, Tyr or Glu; $R_6$ is CML or Leu; $R_7$ is Leu or CML; $R_9$ is Glu, CML, Asn or Lys; $R_{10}$ is Val, CML or Nle; $R_{11}$ is Leu, CML or Ile; $R_{12}$ is Glu or His; $R_{14}$ is Ala, Aib, Thr, or Glu; $R_{15}$ is Arg, Orn or Lys; $R_{16}$ is Ala, Aib or CML; $R_{17}$ is Glu or Asp; $R_{18}$ is Gln, Asn or Lys; $R_{20}$ is Ala or Aib; $R_{21}$ is Gln, Aib or Glu; $R_{23}$ is Ala or Aib; $R_{25}$ is Lys or Orn; $R_{26}$ is Aib, CML or D-CML; $R_{28}$ is Lys, Orn, Arg, Har, CML or Leu; $R_{29}$ is CML, Leu or Tyr; $R_{30}$ is Nle or CML; $R_{31}$ is Glu, Aib or Asp; and $R_{33}$ is Ala, Aib, Ile, Gly, Val, Leu, CML, Nle, Phe, Nva or Gln. One analog of this group which is considered to be particularly biopotent from the standpoint of reducing high ACTH levels is [Aib$^{19,24,32}$]-Astressin B.

A yet further preferred group of CRF antagonists has the formula (including nontoxic salts thereof):

with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

For example, chemical synthesis of a peptide analog from one preferred group may include the initial formation of an intermediate of the following amino acid sequence: $X^1$-Asp($X^5$)-Leu-Thr($X^2$)-D-Phe-$R_5$($X^7$ or $X^5$)-Leu-Leu-Arg($X^3$)-$R_9$($X^5$)-$R_{10}$-Leu-$R_{12}$($X^5$ or $X^8$)-Nle-$R_{14}$($X^2$ or $X^5$)-$R_{15}$($X^3$, $X^6$ or $X^8$)-$R_{16}$-$R_{17}$($X^5$)-$R_{18}$($X^4$ or $X^6$)-$R_{19}$-$R_{20}$-$R_{21}$($X^4$ or $X^5$)-$R_{22}$($X^5$ or $X^8$)-$R_{23}$-$R_{24}$($X^3$ or $X^7$)-$R_{25}$($X^6$ or $X^8$)-$R_{26}$($X^4$)-Arg($X^3$)-$R_{28}$($X^3$ or $X^6$)-$R_{29}$($X^7$)-Nle-$R_{31}$($X^5$)-$R_{32}$($X^2$, $X^4$ or $X^5$)-$R_{33}$($X^4$)-$X^9$ wherein: the R-groups are as hereinbefore defined.

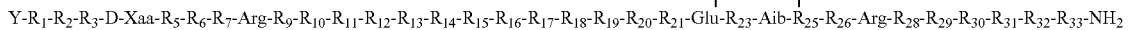

Y-$R_1$-$R_2$-$R_3$-D-Xaa-$R_5$-$R_6$-$R_7$-Arg-$R_9$-$R_{10}$-$R_{11}$-$R_{12}$-$R_{13}$-$R_{14}$-$R_{15}$-$R_{16}$-$R_{17}$-$R_{18}$-$R_{19}$-$R_{20}$-$R_{21}$-Glu-$R_{23}$-Aib-$R_{25}$-$R_{26}$-Arg-$R_{28}$-$R_{29}$-$R_{30}$-$R_{31}$-$R_{32}$-$R_{33}$-$NH_2$ wherein Y is H, Tyr or D-Tyr or an acyl group having up to 15 carbon atoms, preferably up to 12 carbon atoms, and more preferably 1 to 7 carbon atoms, e.g. Ac, For, Acr or Bz; $R_1$ is Asp or des-$R_1$; $R_2$ is Leu or des-$R_2$; $R_3$ is Ser or Thr or des-$R_3$; D-Xaa is D-Phe, D-Leu, D-Tyr, D-Cpa, D-Nal, D-Trp or D-Pal; $R_5$ is His, Tyr or Glu; $R_6$ is CML or Leu; $R_7$ is Leu or CML; $R_9$ is Glu, CML, Asn or Lys; $R_{10}$ is Val, CML, Nle or Met; $R_{11}$ is Leu, CML or Ile; $R_{12}$ is Glu, D-Glu or His; $R_{13}$ is Nle or Met; $R_{14}$ is Ala, D-Ala, Aib, Thr, D-Thr, Glu or D-Glu; $R_{15}$ is Arg, Orn or Lys; $R_{16}$ is Ala, Aib or CML; $R_{17}$ is Glu or Asp; $R_{18}$ is Gln, Asn or Lys; $R_{19}$ is Aib, CMV or CMP; $R_{20}$ is Ala or Aib; $R_{21}$ is Gln, Aib or Glu; $R_{23}$ is Ala or Aib; $R_{25}$ is Lys or Orn; $R_{26}$ is Asn or Aib; $R_{28}$ is Lys, Orn, Arg, Har, CML or Leu; $R_{29}$ is CML, Leu or Tyr; $R_{30}$ is Nle, CML or Met; $R_{31}$ is Glu, Aib or Asp; $R_{32}$ is Aib, CMP or CMV; and $R_{33}$ is Ala, Aib, Ile, Gly, Val, Leu, CML, Nle, Phe, Nva or Gln. Specific analogs of this group which are considered to be particularly biopotent from the standpoint of reducing high ACTH and cortisol levels are:

[CMP$^{19}$, Aib$^{24,32}$]-Astressin B;
[CMP$^{19,32}$, Aib$^{24}$]-Astressin B;
[Aib$^{19,24}$, CMP$^{32}$]-Astressin B;
[CMV$^{19,32}$, Aib$^{24}$]-Astressin B; and
[Aib$^{19,24}$, CMV$^{32}$]-Astressin B.

The peptides are synthesized by a suitable method, such as by exclusively solid-phase techniques, by partial solid-phase techniques, by fragment condensation or by classical solution addition. For example, the method of synthesis disclosed in detail in U.S. Pat. No. 5,777,073 (the disclosure of which is incorporated herein by reference) may be employed. Common to chemical syntheses of peptides is the protection of the labile side chain groups of the various amino acid moieties $X^1$ is either hydrogen or an alpha-amino protecting group. The alpha-amino protecting groups contemplated by $X^1$ are those known to be useful in the art in the step-wise synthesis of polypeptides. Among the classes of alpha-amino protecting groups covered by $X^1$ are (1) acyl-type protecting groups, such as formyl(For), acrylyl(Acr), benzoyl(Bz) and acetyl (Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenyl methyloxycarbonyl (Fmoc), cyclopentyloxy-carbonyl, adamantyloxycarbonyl, and cyclohexyloxy-carbonyl; and (5) thiourethan-type protecting groups, such as phenylthiocarbonyl. The two preferred alpha-amino protecting groups are BOC and Fmoc.

$X^2$ is a protecting group for the hydroxyl group of Thr or Ser and is preferably selected from the class consisting of acetyl(Ac), tert-butyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the guanidino group of Arg or Har preferably selected from the class consisting of nitro, p-toluenesulfonyl(Tos), Z, adamantyloxycarbonyl and BOC, or is hydrogen. Tos is most preferred for the BOC strategy.

$X^4$ is hydrogen or a protecting group, preferably xanthyl (Xan), for the amido group of Asn or Gln. Asn or Gln is often coupled without side chain protection in the presence of hydroxybenzotriazole (HOBt).

$X^5$ is hydrogen or an ester-forming protecting group for the β- or γ-carboxyl group of Asp or Glu, preferably selected from the esters of cyclohexyl (OChx) benzyl (OBzl), 2,6-dichlorobenzyl, methyl, ethyl and t-butyl (Ot-Bu). OChx is preferred for a BOC strategy.

$X^6$ is hydrogen or a protecting group for the side chain amino substituent of Lys or Orn. Illustrative of suitable side chain amino-protecting groups are Z, 2-chlorobenzyloxycarbonyl(2Cl-Z), Tos, t-amyloxycarbonyl(Aoc), BOC and aromatic or aliphatic urethan-type protecting groups as specified hereinbefore. 2Cl-Z is preferred for a BOC strategy.

When His is present, $X^7$ is hydrogen or a protecting group for the imidazole nitrogen such as Tos or 2,4-dinitrophenyl (DNP), and when Tyr is present, $X^7$ is hydrogen or a protecting group for the hydroxyl group such as DCB. When Met is present, the sulfur may be protected, if desired, with oxygen.

The selection of a side chain amino protecting group is not critical except that it should be one which is not removed during deprotection of the alpha-amino groups during the synthesis. Hence, the alpha-amino protecting group and the side chain amino protecting group cannot be the same.

$X^9$ is $NH_2$, a protecting group, such as an ester, or an anchoring bond used in solid phase synthesis for linking to a solid resin support, preferably one of the following:
—NH-benzhydrylamine (BHA) resin support and
—NH-paramethylbenzhydrylamine(MBHA) resin support.
Cleavage from a BHA or MBHA resin directly gives the CRF analog amide. By employing a methyl-derivative of such a resin, a methyl-substituted amide can be created, which is considered to be the equivalent of the unsubstituted amide.

In the amino acid sequence for the intermediate, at least one of $X^1$, $X^2$, $X^3$, $X^4$, $X^5$, $X^6$ and $X^7$ is a protecting group or $X^9$ includes resin support. The particular amino acid chosen for each R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

For the acylated N-terminus, an acyl group having 15 carbon atoms or less is present, preferably 12 or less, as represented by Y; acetyl(Ac), formyl(For), acrylyl(Acr) and benzoyl(Bz) propionyl, butyroyl, valeroyl, hexanoyl, octanoyl, decanoyl, tetradecanoyl, are the preferred acyl groups although to facilitate labeling, an acylating agent containing a hydroxy aryl moiety, such as 4-hydroxy-phenylpropionic acid (des-$NH_2$-Tyr) or 4-hydroxy-phenylacetic acid, may be used. Also, Y may alternatively be a suitable sugar or lipid, which are equivalents that may be used to adjust hydrophilicity.

The peptides of the invention may be synthesized by classical peptide solution synthesis, and such synthesis may be preferred for large quantities. To obtain limited quantities, e.g. less than 1 kg, it may be preferable to prepare them using solid phase synthesis, such as that described by Merrifield, *J. Am. Chem. Soc.*, 85, p 2149 (1964), which facilitates the CRF antagonist peptides being prepared in a straightforward manner and then quickly tested to determine biological activity. This facilitates the ready preparation and evaluation of various CRF antagonist peptides. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for an antagonist based upon human CRF can be prepared by attaching alpha-amino-protected Ile to an MBHA resin.

Ile (R33) protected by BOC is coupled to the MBHA resin using a coupling reagent in methylene chloride and/or dimethylformamide (DMF) and/or N-methyl pyrrolidone (NMP). Following the coupling of BOC-Ile to the resin support, the alpha-amino protecting group is removed, as by using trifluoroacetic acid(TFA) in methylene chloride, TFA alone or with HCl in dioxane. Preferably 50 volume % TFA in methylene chloride is used with 0-5 weight % 1,2 ethanedithiol or m-cresol. The deprotection is carried out at a temperature between about 0° C. and 70° C. Other standard cleaving reagents and conditions for removal of specific alpha-amino protecting groups may be used, as described in Schroder & Lubke, "The Peptides", Vol. 1, 72-75 (Academic Press 1965) and in the well known Barany-Merrifield text.

After removal of the alpha-amino protecting group of Ile, the remaining alpha-amino- and side chain-protected amino acids are coupled stepwise in the desired order to obtain an intermediate compound such as defined hereinbefore. As an alternative to adding each amino acid separately in the synthesis, some of them may be coupled to one another in solution phase prior to addition to the solid phase reactor.

Activating or coupling reagents for use in the solid phase synthesis of the peptides are well known in the peptide art. Examples of such reagents are suitable carbodiimides, such as N,N'-diisopropyl carbodiimide,(DIC) N,N'-dicyclohexyl carbodiimide(DCC) and N-ethyl-N'-(3-dimethylaminopropyl) carbodiimide. Other activating reagents and their use in peptide coupling are described by Schroder & Lubke, supra, in Chapter III and by Kapoor, *J. Phar. Sci.*, 59, pp 1-27 (1970). P-nitrophenyl ester(ONp) can also be used to activate the carboxyl end of Asn or Gln for coupling. For example, BOC-Asn(ONp) can be coupled overnight using one equivalent of HOBt in a 50% mixture of DMF and methylene chloride.

Other more recent coupling reagents include HBTU, TBTU, HATU, BOP and PyBop among others.

Each protected amino acid or amino acid sequence is introduced into the solid phase reactor in about a threefold excess, and the coupling is carried out in a medium of dimethylformamide(DMF):$CH_2Cl_2$ (1:1) or in $CH_2Cl_2$ alone at room temperature. Alternatively, coupling may be carried out at elevated temperature up to about 70° C. in NMP or in a mixture of toluene:DMSO (70:30) or in DMF in a microwave synthesizer. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the alpha-amino protecting group prior to the coupling of the next amino acid. The coupling reactions can be performed automatically, as on a CSBio Model 356 automatic synthesizer, using a program such as that reported in Rivier et al., *Biopolymers*, 17, pp.1927-1938, (1978).

After the desired amino acid sequence has been completed, the intermediate peptide is removed from the resin support unless it is desired to form the cyclizing bond while attached to the resin, as described hereinafter. Removal is effected by treatment with a reagent, such as liquid hydrogen fluoride (HF), which not only cleaves the peptide from the resin but also cleaves all remaining side chain protecting groups $X^2$, $X^3$, $X^4$, $X^5$, $X^6$ and $X^7$ and the alpha-amino protecting group $X^1$, if still present (unless it is an acyl group which is intended to be present in the final peptide), to obtain the peptide. When using hydrogen fluoride for cleaving, anisole or cresol and methylethyl sulfide are included in the reaction vessel as scavengers. When Met is present in the sequence, the BOC protecting group may be cleaved with trifluoroacetic acid (TFA)/ethanedithiol prior to cleaving the peptide from the resin to eliminate potential S-alkylation.

To effect an amide cyclizing linkage (lactam bridge), cyclization may be carried out while the partially protected peptide remains attached to the resin as disclosed in U.S. Pat. Nos. 5,064,939 and 5,043,322, the disclosures of which are incorporated herein by reference. Such a procedure effectively creates an amide cyclizing bond between the two desired side chains while other residues, such as Asp, Glu and/or Lys, in the peptide intermediate retain their side-chain protection.

When cyclizing via an amide bond between a side-chain carboxyl group of the 22-position residue of Astressin B and a side-chain amino group of the 25-position residue, it is preferable to synthesize the protected peptide on an MBHA or BHA resin and to derivatize the benzyl ester of the particular carboxyl acid side chain to the hydrazide while the peptide is still attached to the resin and then react it with a selectively deprotected amino-side chain as set forth in U.S. Pat. No. 5,043,322. Preferably cyclization is accomplished by using a base-labile protecting group, e.g., OFm, for the carboxyl side-chain of the residue to be involved in the amide-bond bridge and using Fmoc as a protecting group for the amino side chain on the other residue that is to be involved. The a-amino protecting group on the residue at the N-terminus of the intermediate and all of the other side-chain protecting groups remain in place while the two base-labile groups are removed using piperidine or the like. Following such selective removal, a reaction to accomplish cyclization is carried out by treating with PyBOP reagent and DIPEA base which effects substantially complete generation of the amide bond. Following cyclization, the peptide is completely deprotected and cleaved from the resin using a reagent, such as HF. Optionally, a BOC-protecting group is first removed from the N-terminus using TFA, particularly if the N-terminus is to be acylated.

Alternatively, cyclizations of peptides by creating such amide linkages can also be effected using teachings of U.S. Pat. No. 4,115,554 (Sep. 19, 1978); U.S. Pat. No. 4,133,805 (Jan. 9, 1979); U.S. Pat. No. 4,140,767 (Feb. 20, 1979); U.S. Pat. No. 4,161,521 (Jul. 17, 1979); U.S. Pat. No. 4,191,754 (Mar. 4, 1980); U.S. Pat. No. 4,238,481 (Dec. 9, 1980); U.S. Pat. No. 4,244,947 (Jan. 13, 1981); and U.S. Pat. No. 4,261,885 (Apr. 14, 1981).

A straightforward in vitro assay can be carried out using rat anterior pituitary cells in monolayer culture to determine what CRF-activity a candidate peptide will exhibit; the procedure which is used is that generally set forth in *Endocrinology*, 91, 562 (1972). The assay will show whether a candidate peptide will exhibit some activity as a CRF agonist and stimulate ACTH secretion by activating CRF receptors on such cells; in this manner its intrinsic CRF activity is measured via the use of high doses. Essentially the same in vitro assay is employed to determine whether the candidate will exhibit strong CRF antagonistic properties when administered together with a challenge dose of CRF, usually either oCRF or r/hCRF.

A candidate CRF antagonist peptide is also readily evaluated in a binding assay using a known CRF receptor, such as that described in Perrin, M., et al., *Endocrinology*, 118, 1171-1179 (1986). The details of binding assays are discussed later in this specification and may be carried out with human CRF-R. Radioligands such as (cyclo 30-33)[$I^{125}$-D-Tyr$^{12}$, Glu$^{30}$, Lys$^{33}$, Nle$^{21,38}$]-r/hCRF(12-41) and its analog having D-His$^{32}$, have high affinity for human CRF-R. For example, the first-named compound has a $K_D$ of 2.0 nanomolar (1.4-2.9) for binding to hCRF-R1, which is essentially equal to that of the comparable D-Phe$^{12}$ analog. One such representative binding assay utilizing CRF-R receptor is described in Chen, et al., *P.N.A.S.*, 90, 8967-8971 (October 1993). Because certain of these cyclic peptides exhibit high binding affinity for all known CRF receptors, they are especially valuable for use in screening assays. Such assays are advantageously used to screen for potential CRF-like ligands, in peptide or other form, using such a labeled cyclic CRF antagonist with high affinity.

The following Example I sets forth a preferred method for synthesizing CRF antagonists by the solid-phase technique with BOC strategy.

EXAMPLE I

The synthesis of [D-Aph(Cbm)$^{24}$]-Astressin B having the amino acia sequence:

Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-D-Aph(Cbm)-Lys-Asn-Arg-Lys-Leu-Nle-Glu-CML-Ile-NH$_2$ is conducted in a stepwise Synthesis of cyclo(30-33)[DPhe$^{12}$,Nle$^{21,38}$,Leu(Me)$^{27,40}$,Glu$^{30}$,DAph(Cbm)$^{32}$,Lys$^{33}$]Ac-hCRF (9-41); [DAph(Cbm)$^{24}$]Astressin B It was synthesized by solid phase methodology in a stepwise manner on an MBHA resin using the BOC strategy with orthogonal protection (Fmoc and OFm) of the side chains of residues to be cyclized Amino acid derivatives Boc-Ala-OH, Boc-Arg(Tos)-OH, Boc-Asn(Xan)-OH, Boc-Asp (cHex)-OH, Boc-Gln(Xan)-OH, Boc-Glu(cHex)-OH, Boc-His(Dnp)-OH, Boc-Ile-OH, Boc-Nle-OH, Boc-Leu-OH, Boc-Phe-OH, Boc-Pro-OH, Boc-Ser(Bzl)-OH, Boc-Thr(Bzl)-OH, Boc-Tyr(2-Br-Cbz)-OH, and Boc-Val-OH were obtained from Bachem Inc. (Torrance, Calif.), Chem-Impex International (Wood Dale, Ill.), Novabiochem (San Diego, Calif.), Reanal (Budapest, Hungary), and AApptec (Louisville, Ky.). Boc-Leu(Me)-OH, {Hernandez, 1993 #1970} Boc-DAph(Cbm)-OH {Jiang, 2001 #2828} were synthesized as described earlier. All solvents were reagent grade or better. The peptide synthesizer was the product of CSBio (Model 356). TFA containing 1% m-cresol was used to remove the Boc group. DIC/HOBt mediated the main chain assembly. 1.6 mM (four-fold excess) of protected amino acid was used based on the original substitution of the MBHA resin (0.4 mM/g). Coupling time was 60 min but a re-coupling of Boc-Glu(cHex)-OH and Boc-Gln(Xan)-OH was applied after residues 32 (CML) and 19 (CML), respectively. Acetylation of the N-terminus was carried out after completion of the sequence with excess of acetic anhydride in DCM for 15 min. The DNP protecting group of the side chain of histidine was cleaved with 20% thiophenol in NMP for 3 hours. Deprotection of the Fmoc group of residue 33 (Lys) side chain and the OFm group of residue 30 (Glu) side chain was achieved simultaneously using a solution of 20% piperidine/NMP (2×10 min) followed by sequential washes with NMP, MeOH, 10% TEA/DCM, and DCM. Lactam formation was mediated using PyBop and DIPEA in NMP for several hours at room temperature till it showed negative ninhydrin test.

The peptide was cleaved and deprotected by anhydrous HF in the presence of anisole (5-10% v/v) at 0° C. for 90 min. The crude peptide was precipitated and washed with anhydrous diethyl ether, filtered, extracted from the resin with a solution of 0.1% TFA in $CH_3CN/H_2O$ (60:40), and lyophilized. The peptide was purified using RP-HPLC and three solvent systems (TEAP at pH 2.25, TEAP at pH 6.5, and 0.1% TFA, successively). A linear gradient 0.3% B per 1 min increases from the baseline % B (Eluent A=TEAP at pH 2.25, eluent B=60% $CH_3CN$, 40% A) was used in the first purification step, followed by a second purification step using a linear gradient 1% B per 1 min increases from the baseline % B (Eluent A=TEAP at pH 6.5, eluent B=60% $CH_3CN$, 40% A).

The peptide was desalted during the third purification stage by a linear gradient 1% B per 1 min increases from the baseline % B (Eluent A=0.1% TFA, eluent B=60% $CH_3CN$, 40% A). Fractions of each run were tested by analytical RP-HPLC using isocratic conditions (45% $CH_3CN$/55% $H_2O$ containing 0.1% TFA) on a Grace Vydac $C_{18}$ column. After the final purification step, the good quality fractions were pooled and lyophilized. The purity of the peptide was determined with capillary zone electrophoresis (CZE) using a Beckman P/ACE System 2050 controlled by an IBM Personal System/2 model 50Z and using a ChromJet integrator. Field strength of 15 kV at 30° C., mobile phase: 100 mM sodium phosphate (85:15, H2O:CH3CN) pH 2.50, on a Supelco P175 capillary (363 μm OD×75 μm ID×50 cm length). It was 85% pure. The purity by analytical HPLC was 78% (RT=25.87 min) RP-HPLC was performed using a GE Healthcare AKTApurifier 10 and a Phenomenex Kinetex XB-C18 column (4.6×100 mm, 2.6 μm particle size, 100 Å pore size). The solvent system was comprised of eluent A=0.015M TEAP, pH 6.5, eluent B=60% $CH_3CN$, 40% A. A gradient was performed from 50% B to 90% B in 40 min (hold at 90% B), at a flow rate of 1.2 mL/min. Detection was at 214 nm. MS analysis of the product shows an $[M+H]^+$ mass of 4030.17 Da, which coincides with the calculated value of 4029.28 Da.

In vitro biopotency of the product peptide can be measured as follows. Rat anterior pituitary glands from male Sprague-Dawley rats are dissociated by collagenase and plated (0.16× $10^6$ cells/well in 48-well plates) in medium containing 2% fetal bovine serum (FBS). Three days after plating, the cells are washed three times with fresh medium containing 0.1% bovine serum albumin (BSA) and incubated for 1 hour. Following the 1 hour preincubation, the cells are washed once more, and the test peptides are applied in the presence of 1 nM oCRF. At the end of a 3 hour incubation period the media are collected and the level of ACTH is determined by radioimmunoassay (Diagnostic Products Corporation).

Administration of the peptide inhibits the secretion of ACTH and β-endorphin-like immunoactivities (β-END-LI) and exhibits especially long duration of inhibition. The in vivo assays which are employed to test these CRF antagonists use adrenalectomized (ADX) rats. Adult male Sprague Dawley rats (230-250 g) are adrenalectomized via a lombar approach under halothane anesthesia. Their diet is supplemented with 0.9% NaCl in the drinking water and with oranges. Two days prior to the experiments, the animals are equipped with jugular cannulae, as described in C. Rivier, et al., *Endocrinology*, 110, 272-278 (1982). On the morning of the experiments, the i.v. cannulae are connected to a line filled with heparinized saline, and the rats are placed in individual buckets and left undisturbed for 2 hours. For the experiment, a first blood sample of 0.3 mL is withdrawn, the test solution is injected (in an 0.2-0.5 mL volume), and subsequent blood samples are obtained at about 15, 45, 90 and 120 minutes. The blood samples are centrifuged, and the separated plasma are kept frozen (−20° C.) until assayed for ACTH values. Plasma ACTH levels are measured as described in C. Rivier, et al. *J. Neuroscience*, 14, 1985 (1994).

As a result of in vivo testing at a level of 1 mg/kg of body weight, it is shown that, at 15 minutes time, the cyclic CRF antagonist is more effective than the standard CRF antagonist in reducing ACTH levels in the serum. At 45 minutes following injection, the cyclic compound depresses the ACTH levels even further than at the 15 minute level, while the effect of the standard CRF antagonist has run its course and levels are substantially the same as in the control animals. At 90 minutes, the ACTH levels remain at about this low level for those rats treated with the cyclic compound, well below the level of the control rats and those treated with the standard CRF antagonist. At 120 minutes following injection, the level of ACTH is essentially back to normal. When tested at levels of 0.3 mg/kg of body weight, the results are essentially the same for 15 and 45 minutes; however, at 90 minutes, there is still some improvement over the rats treated with the standard CRF antagonist but it is not as significant as shown when injected at a level of 1 milligram per kg of body weight.

One further series of tests is carried out where rats are injected with the standard CRF antagonist at a level of 3 mg/kg and 2 sets of other rats are injected with the cyclic CRF antagonists at levels of 0.1 mg/kg and 0.03 mg/kg. The results are essentially the same as in the previous two tests at 15 and 45 minutes, with even the 0.03 mg/kg injection showing improvement over the 3 mg/kg injection of the standard CRF antagonist. At 90 minutes, there is additional improvement over the rats injected with the 3 mg/kg of the standard; however, the ACTH levels essentially return to about the levels at the beginning of the test upon the passage of 90 minutes. Tests show that, even when used at a level 1/100 of the amount of the standard CRF antagonist, the cyclic compound still performs substantially better over a 45-minute time span. Collectively, these data show that the cyclic peptide is long acting. Upon subcutaneous (s.c.) administration in vivo, it is substantially longer acting than Astressin B.

The peptide has also been evaluated in binding assay. The binding affinities (Ki, nM) of the peptide to cell membranes expressing either CRFR1 or CRFR2 in the presence of a standard were measured. The values were derived from competitive radioligand displacement assays using the nonselective $^{125}$I-labeled agonist [$Tyr^0$, $Glu^1$,$Nle^{17}$]-sauvagine as the radioligand and crude membrane fractions from COSM6 cells transiently expressing the respective receptors. Briefly, 200 000 cpm (ca. 0.5 nM)$^{125}$I-[$Tyr^0$,$Glu^1$,$Nle^{17}$]-sauvagine were combined with increasing concentrations of peptide (initially diluted at 10 mg/mL in DMSO) from 0.1 to 1000 nM in 0.2 mL assay buffer (50 mM Na Hepes, pH 7.5; 10 mM MgCl2; 2 mM EGTA; 0.1% BSA) and incubated for 90 min at 20° C. Reactions were performed in 96-well Multi-Screen plates (Millipore, Bedford, Mass.) with GF/C filters. Binding was terminated by aspiration through the plate, followed by a 0.2-ml wash with assay buffer. All assays contained tubes for nonspecific binding, which was taken to be the counts per minute remaining in the presence of 100 to 200 nM unlabeled ligand. $K_{is}$ and their 95% confidence limits were determined by pooling data from at least three independent assays using the LIGAND computer program. [Munson P J and Rodbard D (1980) Ligand: A versatile computerized approach for characterization of ligand-binding systems. *Anal Biochem* 107: 220-239]. The cyclic peptide product of the above described synthesis exhibits biopotency about 1.3 times greater for CRFR1 and about 3 times greater for CRFR2 than that of the present "Standard" peptide, i.e., Astressin B.

EXAMPLE I A

The synthesis of Example I is repeated using a triple batch but shortening the peptide at the N-terminus ⅓ of the original amount of resin is removed following the addition of D-Phe and then following the addition of Thr; the synthesis is terminated after the addition of Leu. Following cleavage, the following three peptides are produced:
[D-Aph(Cbm)$^{24}$] Astressin B (2-33);
[D-Aph(Cbm)$^{24}$] Astressin B (3-33); and
[D-Aph(Cbm)$^{24}$] Astressin B (4-33).

The biopotency of each peptide is measured in vitro, as previously described, compared to the laboratory standard peptide, i.e., Astressin B. The results are generally comparable to the peptide of Example I but show slightly less biopotency.

EXAMPLE II

The synthesis of Example I is repeated, substituting CML for D-Aph(Cbm), to produce the following peptide:
[CML$^{24}$]-Astressin B. It has the amino acid sequence:

Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-CML-Lys-Asn-Arg-Lys-Leu-Nle-Glu-
-CML-Ile-NH$_2$

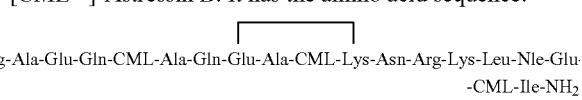

MS analysis of the product shows an [M+H]$^+$ mass of 3951.33 Da, which coincides with the calculated value of 3951.29 Da. It has a purity of about 77%, as confirmed by CZE and 90% as confirmed by HPLC (RT=27.04 min) The peptide's biopotency, determined as previously described, is about equal that of the present laboratory Standard, i.e., Astressin B, on CRFR1 and twice as potent on CRFR2.

EXAMPLE II A

The synthesis of Example II is repeated, substituting D-CML for CML, to produce the following peptide:
[D-CML$^{24}$]-Astressin B. It has the amino acid sequence:

Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-D-CML-Lys-Asn-Arg-Lys-Leu-Nle-Glu-
-CML-Ile-NH$_2$

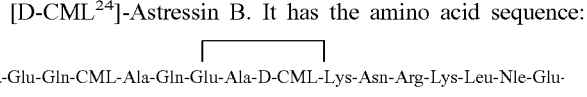

MS analysis of the product shows an [M+H]$^+$ mass of 3951.59 Da, which coincides with the calculated value of 3951.29 Da. It has a purity of about 75% as confirmed by CZE and 84% as confirmed by HPLC (RT=28.14 min) The peptide's biopotency, determined as previously described, is about equal that of the laboratory Standard, i.e., Astressin B.

EXAMPLE II B

The synthesis of Example II is repeated, substituting D-Aph(Hor) for CML, to produce the following peptide:
[D-Aph(Hor)$^{24}$]-Astressin B. It has the amino acid sequence:

Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-D-Aph(Hor)-Lys-Asn-Arg-Lys-Leu-Nle-Glu-
-CML-Ile-NH$_2$.

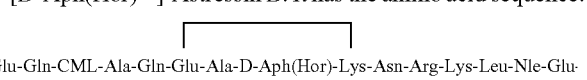

The peptide's biopotency is about equal to that of the laboratory Standard, i.e., Astressin B.

EXAMPLE III

The synthesis of [CMP$^{19}$, Aib$^{24,32}$]-Astressin B having the amino acid sequence:

Asp-Leu-Thr-D-Phe-His-Leu-Leu-Arg-Glu-Val-Leu-Glu-Nle-Ala-Arg-Ala-Glu-Gln-CMP-Ala-Gln-Glu-Ala-Aib-Lys-Asn-Arg-Lys-Leu-Nle-Glu-Aib-Ile-NH$_2$

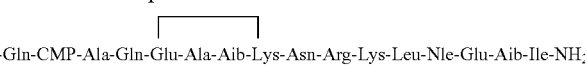

is conducted as described in Example I above, except that residue 19 is CMP instead of CML, and residues 24 and 32 are Aib instead of D-Aph(Cbm) and CML.

MS analysis of the product shows an [M+H]⁺ mass of 3901.08 Da, which coincides with the calculated value of 3901.18 Da. It has a purity of about 99%, further confirmed by CZE and 94% by HPLC (RT=23.57 min) The peptide's biopotency, determined as previously described, is about equal that of the laboratory Standard, i.e., Astressin B.

EXAMPLE III A

The general synthesis of Example I is used to produce the following peptide: [CMP$^{19,32}$, Aib$^{24}$]-Astressin B having the amino acid sequence:

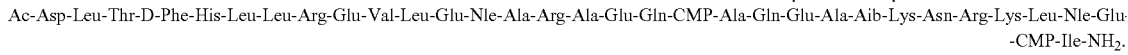

Ac-Asp-Leu-Thr-D-Phe-His-Leu-Leu-Arg-Glu-Val-Leu-Glu-Nle-Ala-Arg-Ala-Glu-Gln-CMP-Ala-Gln-Glu-Ala-Aib-Lys-Asn-Arg-Lys-Leu-Nle-Glu-CMP-Ile-NH$_2$.

MS analysis of the product shows an [M+H]⁺ mass of 3977.76 Da, which coincides with the calculated value of 3977.21 Da. It has a purity of about 95% as confirmed by CZE and 77% by HPLC (RT=26.92 min). The peptide's biopotency, determined as previously described, is about one-half times that of the standard peptide, Astressin B on CRFR1 and the same on CRFR2.

EXAMPLE III AA

The general synthesis of Example I is used to produce the following peptide: [CMP$^{19}$, Aib$^{24}$]-Astressin B having the amino acid sequence:

Ac-Asp-Leu-Thr-D-Phe-His-Leu-Leu-Arg-Glu-Val-Leu-Glu-Nle-Ala-Arg-Ala-Glu-Gln-CMP-Ala-Gln-Glu-Ala-Aib-Lys-Asn-Arg-Lys-Leu-Nle-Glu-CML-Ile-NH$_2$.

The peptide's biopotency, determined as previously described, is greater than the standard peptide, Astressin B.

EXAMPLE III B

The general synthesis of Example I is used to produce the following peptide: [Aib$^{19,24}$, CMP$^{32}$]-Astressin B having the amino acid sequence:

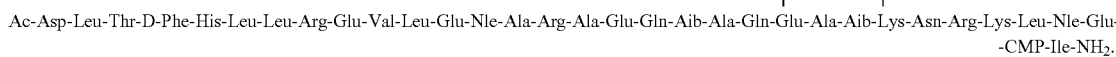

Ac-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg-Lys-Leu-Nle-Glu-CMP-Ile-NH$_2$.

MS analysis of the product shows an [M+H]⁺ mass of 3901.18 Da, which coincides with the calculated value of 3901.18 Da. It has a purity of about 84% as confirmed by CZE and 80% by HPLC (RT=24.18 min). The peptide's biopotency, determined as previously described, is about three times less potent on CRFR1 and 1.3 times more potent than that of the standard peptide, Astressin B.

EXAMPLE III C

The general synthesis of Example I is used to produce the following peptide: [CMV$^{19,32}$, Aib$^{24}$]-Astressin B, having the amino acid sequence:

Ac-Asp-Leu-Thr-D-Phe-His-Leu-Leu-Arg-Glu-Val-Leu-Glu-Nle-Ala-Arg-Ala-Glu-Gln-CMV-Ala-Gln-Glu-Ala-Aib-Lys-Asn-Arg-Lys-Leu-Nle-Glu-CMV-Ile-NH$_2$.

MS analysis of the product shows an [M+H]$^+$ mass of 3881.19 Da, which coincides with the calculated value of 3881.22 Da. It has a purity of about 95% as confirmed by CZE and 91% by HPLC (RT=23.82 min). The peptide's biopotency, determined as previously described, is about two times less potent on CRFR1 and 10 times more potent on CRFR2 than that of the standard peptide, Astressin B.

EXAMPLE III D

The general synthesis of Example I is used to produce the following peptide: [Aib$^{19,24}$, CMV$^{32}$]-Astressin-B having the amino acid sequence:

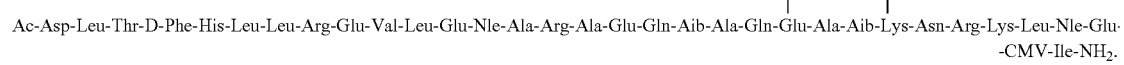
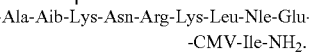

Ac-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg-Lys-Leu-Nle-Glu-
-CMV-Ile-NH$_2$.

MS analysis of the product shows an [M+H]$^+$ mass of 3853.05 Da, which coincides with the calculated value of 3853.18 Da. It has a purity of about 97% as confirmed by CZE and 90% by HPLC (RT=22.06 min). The peptide's biopotency, determined as previously described, is about half at CRFR1 and three times at CRFR2 than that of the standard peptide, Astressin B.

EXAMPLE III E

The general synthesis of Example I is used to produce the following peptide: [Aib$^{19,24,32}$]-Astressin B, having the amino acid sequence:

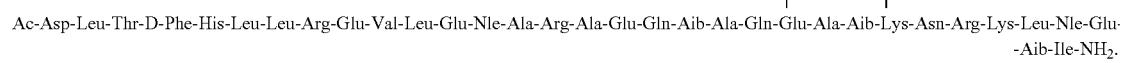
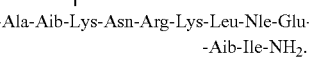

Ac-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg-Lys-Leu-Nle-Glu-
-Aib-Ile-NH$_2$.

MS analysis of the product shows an [M+H]$^+$ mass of 3824.98 Da, which coincides with the calculated value of 3825.15 Da. It has a purity of about 96% as confirmed by CZE and 98% by HPLC (RT=19.95 min). The peptide's biopotency, determined as previously described, is about four times less potent at CRFR1 and four times more potent at CRFR2 than that of the standard peptide, Astressin B.

Various of the peptides from these examples are tested for solubility and in binding assay. The solubility study is carried out in DMSO (20%) and 5% D-mannitol in water (80%) with the peptide concentration of 10 mg/mL. Results are set forth in the Table 1 below.

TABLE 1

| Peptide of Example | Solubility | | | Binding Affinity | |
|---|---|---|---|---|---|
| | 5 min | 2 h | 24 h | CRFR1 | CRFR2 |
| IIIE | Sol. | Sol. | Sol. | 1.17 (0.882-1.56) | 0.32 (0.173-0.60) |
| IIID | Sol. | Sol. | Sol. | 0.7 (0.4-1.3) | 0.39 (0.29-0.52) |
| IIIC | Sol. | Gel | Gel | 0.68 (0.36-1.29) | 0.13 (0.021-0.84) |
| II | Sol. | Sol. | Sol. | 0.32 (0.20-0.51) | 0.60 (0.60-0.90) |
| IIA | Sol. | Sol. | Sol. | 0.3 (0.07-1.1) | 0.46 (0.27-0.79) |

TABLE 1-continued

| Peptide of Example | Solubility | | | Binding Affinity | |
|---|---|---|---|---|---|
| | 5 min | 2 h | 24 h | CRFR1 | CRFR2 |
| III | Sol. | Sol. | Sol. | 0.49 (0.23-1.06) | 0.86 (0.66-1.1) |
| IIIA | Insol. | Insol. | Insol. | 0.79 (0.24-2.60) | 1.23 (1-1.5) |
| IIIB | Sol. | Sol. | Sol. | 0.91 (0.18-4.7) | 0.89 (0.50-1.6) |
| I | Sol. | Sol. | Sol. | 0.22 (0.15-0.33) | 0.44 (0.253-0.76) |

Note:
The Binding Affinity studies were carried out using a Sauvagine tracer.

EXAMPLE III EA

The general synthesis of Example III E is repeated with one change. Acylation of the N-terminus was carried out, after completion of the sequence, using a molar excess of >100 times of propionic acid in CH$_2$Cl$_2$ with DIC activation for 15 minutes. The following peptide is produced: [Aib$^{19,24,32}$]-Propionyl-Astressin B, having the amino acid sequence:

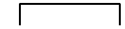
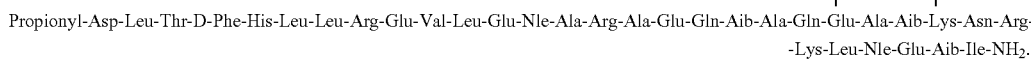

Propionyl-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg-
-Lys-Leu-Nle-Glu-Aib-Ile-NH$_2$.

MS analysis of the product shows an [M+H]+ mass of 3839.19 Da, which coincides with the calculated value of 3839.14 Da. It has a purity of about 99% as confirmed by CZE and 96% by HPLC (RT=17.12 min). The peptide's biopotency, determined as previously described, is one-half as potent at CRFR1 and four times better at CRFR2 than that of the standard peptide, Astressin B.

EXAMPLE III EB

The general synthesis of Example III E is repeated with one change. Acylation of the N-terminus was carried out, after completion of the sequence, using an excess of butyric anhydride in $CH_2Cl_2$ for 15 minutes. The following peptide is produced: [Aib$^{19,24,32}$]-Butyroyl-Astressin B, having the amino acid sequence:

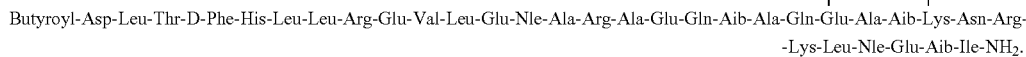

Butyroyl-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg--Lys-Leu-Nle-Glu-Aib-Ile-NH$_2$.

MS analysis of the product shows an [M+H]+ mass of 3853.02 Da, which coincides with the calculated value of 3853.14 Da. It has a purity of about 94% as confirmed by CZE and 96% by HPLC (RT=18.60 min). The peptide's biopotency, determined as previously described, is one-half as potent on CRFR1 and four times better on CRFR2 than that of the standard peptide, Astressin B.

EXAMPLE III EC

The general synthesis of Example III E is repeated with one change. Acylation of the N-terminus was carried out, after completion of the sequence, using an excess of valeroic acid in $CH_2Cl_2$ with DIC activation for 15 minutes. The following peptide is produced: [Aib$^{19,24,32}$]-Valeroyl-Astressin B, having the amino acid sequence:

Valeroyl-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg--Lys-Leu-Nle-Glu-Aib-Ile-NH$_2$.

MS analysis of the product shows an [M+H]+ mass of 3867.20 Da, which coincides with the calculated value of 3867.14 Da. It has a purity of about 98% as confirmed by CZE and 95% by HPLC (RT=20.36 min). The peptide's biopotency, determined as previously described, is one-half as potent at CRFR1 and four times better at CRFR2 than that of the standard peptide, Astressin B.

EXAMPLE III ED

The general synthesis of Example III E is repeated with one change. Acylation of the N-terminus was carried out, after completion of the sequence, using an excess of hexanoic acid in $CH_2Cl_2$ with DIC activation for 15 minutes. The following peptide is produced: [Aib$^{19,24,32}$]-Hexanoyl-Astressin B, having the amino acid sequence:

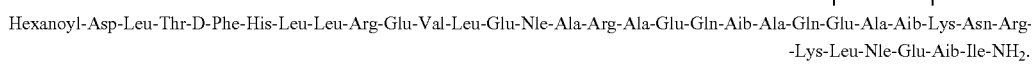

Hexanoyl-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg--Lys-Leu-Nle-Glu-Aib-Ile-NH$_2$.

MS analysis of the product shows an [M+H]⁺ mass of 3881.89 Da, which coincides with the calculated value of 3881.20 Da. It has a purity of about 99% as confirmed by CZE and 84% by HPLC (RT=22.54 min). The peptide's biopotency, determined as previously described, is one-half as potent for CRFR1 and four times more potent at CRFR2 than that of the standard peptide, Astressin B.

EXAMPLE III EE

The general synthesis of Example III E is repeated with one change. Acylation of the N-terminus was carried out, after completion of the sequence, using an excess of decanoic acid in CH$_2$Cl$_2$ with DIC activation for 15 minutes. The following peptide is produced: [Aib$^{19,24,32}$]-Decanoyl-Astressin B, having the amino acid sequence:

Decanoyl-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg--Lys-Leu-Nle-Glu-Aib-Ile-NH$_2$.

MS analysis of the product shows an [M+H]⁺ mass of 3937.10 Da, which coincides with the calculated value of 3937.89 Da. It has a purity of about 91% as confirmed by CZE and 88% by HPLC (RT=31.17 min). The peptide's biopotency, determined as previously described, is one-half as potent at CRFR1 and four times more potent at CRFR2 than that of the standard peptide, Astressin B.

EXAMPLE III EF

The general synthesis of Example III E is repeated with one change. Acylation of the N-terminus was carried out, after completion of the sequence, using an excess of tetradecanoic acid in CH$_2$Cl$_2$ with DIC activation for 15 minutes. The following peptide is produced: [Aib$^{19,24,32}$]-Tetradecanoyl-Astressin B, having the amino acid sequence:

Tetradecanoyl-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg-Lys-Leu-Nle-Glu-Aib-Ile-NH$_2$.

MS analysis of the product shows an [M+H]⁺ mass of 3994.29 Da, which coincides with the calculated value of 3993.89 Da. It has a purity of about 96% as confirmed by CZE and 92% by HPLC (RT=41.83 min). The peptide's biopotency, determined as previously described, is 2.5 times less potent at CRFR1 and two times less potent at CRFR2 than that of the standard peptide, Astressin B.

EXAMPLE III EG

The general synthesis of Example III E is repeated with one change. Acylation of the N-terminus was carried out, after completion of the sequence, using an excess of 21-amino-4,7,10,13,16,19-hexaoxaheneicosanoic acid in CH$_2$Cl$_2$ with DIC activation for 15 minutes. The following peptide produced: [Aib$^{19,24,32}$]21-amino-4,7,10,13,16,19-hexaoxaheneicosanoyl -Astressin B, having the amino acid sequence:

21-amino-4, 7, 10, 13, 16, 19-hexaoxaheneicosanoyl-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg-Lys-Leu-Nle-Glu-Aib-Ile-NH$_2$.

MS analysis of the product shows an [M+H]⁺ mass of 4118.55 Da, which coincides with the calculated value of 4117.38 Da. It has a purity of about 88% as confirmed by CZE and 84% by HPLC (RT=14.66 min). The peptide's biopotency, determined as previously described, is ten times less potent at CRFR1 and slightly less potent on CRFR2 than that of the standard peptide, Astressin B.

Various of the peptides from these examples are tested for solubility and in binding assay. The solubility study is carried out in DMSO (20%) and 5% D-mannitol in water (80%) with the peptide concentration of 10 mg/mL. Results are set forth in the Table 2 below.

TABLE 2

| Peptide of | Solubility | | | Binding Affinity | |
|---|---|---|---|---|---|
| Example | 2 min | 5 min | 2 h | CRFR1 | CRFR2 |
| IIIEA | Sol. | Sol. | Sol. | 0.69 (0.57-0.83) | 0.36 (0.32-0.41) |
| IIIEB | Slightly Sol. | Sol. | Sol. | 0.74 (0.58-0.94) | 0.35 (0.28-0.43) |
| IIIEC | Slightly Sol. | Slightly Sol. | Sol. | 0.67 (0.50-0.89) | 0.32 (0.27-0.39) |
| IIIED | Insol. | Insol. | Sol. | 0.56 (0.37-0.85) | 0.35 (0.29-0.42) |
| IIIEE | Insol. | Insol. | Slightly Sol. | 0.47 (0.17-1.29) | 0.39 (0.31-0.49) |
| IIIEF | Insol. | Insol. | Insol. | 0.81 (0.60-1.10) | 2.16 (1.91-2.45) |
| IIIEG | Very Sol. | Very Sol. | Very Sol. | 3.4 (2.36-3.82) | 1.71* (1.12-2.59) |

Note:
The Binding Affinity studies were carried out using a Sauvagine tracer.
*This Binding Affinity study was carried out using an Astressin tracer.

EXAMPLE IV

The synthesis of Example II is repeated, but elongating the N-terminus by adding Tyr to produce the following peptide: [Tyr-Asp$^1$, Aib$^{19,24,32}$]-Astressin B, having the amino acid sequence:

Tyr-Asp-Leu-Thr-D-Phe-His-Leu-Leu-Arg-Glu-Val-Leu-Glu-Nle-Ala-

Arg-Ala-Glu-Gln-Aib-Ala-Gln-Glu-Ala-Aib-Lys-Asn-Arg-Lys-Leu-Nle-Glu-Aib-Ile-NH₂.

Administration of the peptide inhibits the secretion of ACTH and β-END-LI. The peptide is readily radiolabeled using $^{125}$I.

EXAMPLE V

The synthesis of [Aib$^{19,24,32}$, Orn$^{25}$]-Astressin B having the amino acid sequence:

Ac-Asp-Leu-Thr-D-Phe-His-Leu-Leu-Arg-Glu-Val-Leu-Glu-Nle-Ala-

Arg-Ala-Glu-Gln-Aib-Ala-Gln-Glu-Ala-Aib-Orn-Asn-Arg-Lys-Leu-Nle-Glu-Aib-Ile-NH₂ is conducted as described in Example IIIE above, except that residue 25 is Orn instead of Lys.

Administration of each of the peptide antagonists inhibits the secretion of ACTH and corticosterone.

EXAMPLE VI A

A 33-residue peptide based upon the amino acid sequence of Carp Urotensin 1(9-41) is synthesized having the formula:

Ac-Asp-Leu-Thr-D-Phe-His-Leu-Leu-Arg-Asn-Nle-Ile-Glu-Nle-Ala-Arg-

Asn-Glu-Asn-Aib-Arg-Glu-Glu-Ala-Aib-Lys-Asn-Arg-Lys-Tyr-Leu-Asp-Aib-Val-NH₂.

Testing in accordance with the general procedure set forth in Example I shows that the cyclic compound inhibits the secretion of ACTH and corticosterone.

EXAMPLE VI B

A 33-residue peptide based upon the amino acid sequence of sauvagine (8-40) having the formula:

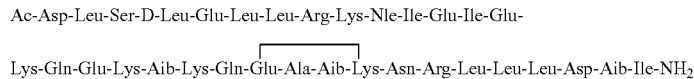

Ac-Asp-Leu-Ser-D-Leu-Glu-Leu-Leu-Arg-Lys-Nle-Ile-Glu-Ile-Glu-Lys-Gln-Glu-Lys-Aib-Lys-Gln-Glu-Ala-Aib-Lys-Asn-Arg-Leu-Leu-Leu-Asp-Aib-Ile-NH$_2$ is synthesized. Testing in accordance with the general procedure set forth in Example I shows that the cyclic compound inhibits the secretion of ACTH and corticosterone.

EXAMPLE VI C

A 33-residue peptide based upon the amino acid sequence of ovine CRF(9-41) having the formula:

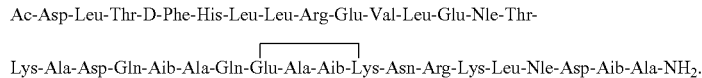

Ac-Asp-Leu-Thr-D-Phe-His-Leu-Leu-Arg-Glu-Val-Leu-Glu-Nle-Thr-Lys-Ala-Asp-Gln-Aib-Ala-Gln-Glu-Ala-Aib-Lys-Asn-Arg-Lys-Leu-Nle-Asp-Aib-Ala-NH$_2$.

Testing in accordance with the general procedure set forth in Example I shows that the cyclic compound inhibits the secretion of ACTH and corticosterone.

EXAMPLE VI D

A 33-residue peptide based upon the amino acid sequence of Sucker Urotensin I(9-41) having the formula:

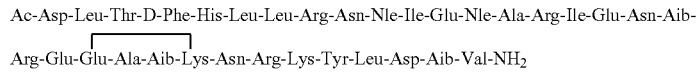

Ac-Asp-Leu-Thr-D-Phe-His-Leu-Leu-Arg-Asn-Nle-Ile-Glu-Nle-Ala-Arg-Ile-Glu-Asn-Aib-Arg-Glu-Glu-Ala-Aib-Lys-Asn-Arg-Lys-Tyr-Leu-Asp-Aib-Val-NH$_2$ is synthesized.

The peptide has biopotency to inhibit the secretion of ACTH and corticosterone.

EXAMPLE VII

Using the procedure as generally set forth in Example I, the following CRF antagonist peptides are also prepared:

[Dpg$^{19,24,32}$]-Astressin B
[Aph(Cbm)$^{24}$]-Astressin B
[Aib$^{19,26}$]-Astressin B
[Dpg$^{19,24}$]-Astressin B
[Aib$^{19,24}$]-Astressin B
[Nle$^{10}$, D-CMP$^{19}$, Aib$^{24}$]-Astressin B
[D-CMP$^{19}$, Aib$^{24}$, CML$^{28}$]-Astressin B
[CML$^{11}$, D-CMP$^{19}$, Aib$^{24}$]-Astressin B
[Asp$^{17}$, D-CMP$^{19}$, Aib$^{24}$]-Astressin B
[Lys$^{15}$, D-CMP$^{19}$, Aib$^{24}$]-Astressin B
[CMV$^{19}$, Aib$^{24}$]-Astressin B
[CMV$^{19}$, Aib$^{24}$, CML$^{29}$]-Astressin B
[CMV$^{19}$, Aib$^{24}$]-Astressin B
[Nle$^{10}$, CMV$^{19}$, Aib$^{24}$]-Astressin B
[CMV$^{19}$, Aib$^{24,26}$]-Astressin B
[CML$^{6}$, Aib$^{19,24,32}$]-Astressin B
[Aib$^{14,19,24,32}$]-Astressin B
[Nle$^{10}$, Aib$^{19,24,32}$]-Astressin B
[CML$^{11}$, Aib$^{19,24,32}$]-Astressin B
[His$^{13}$, Aib$^{19,24,32}$]-Astressin B
[Aib$^{19,24,32}$, CMP$^{28}$]-Astressin B
[Aib$^{19,21,24}$, CMP$^{32}$]-Astressin B
[Aib$^{19,24,26}$, CMP$^{32}$]-Astressin B
[Lys$^{15}$, Aib$^{19,24}$, CMP$^{32}$, CML$^{29}$,]-Astressin B
[Aib$^{19,24,31}$, CMP$^{32}$]-Astressin B
[Aib$^{19,24}$, CMP$^{32}$, CML$^{28}$,]-Astressin B These peptides are biopotent in inhibiting the secretion of ACTH and corticosterone in response to various stimuli, and bind to CRFR1 and CRFR2.

Preferably the cyclic CRF antagonist does not inherently activate the CRF receptor. For example, Peptide I of Example I has only about 3% or less intrinsic CRF activity when administered at the highest dosage. Generally a peptide is considered not to significantly activate the CRF receptor when its intrinsic activity measures about 20% or less of the native compound. Preferred antagonists have an intrinsic activity of about 15% or less; however, intrinsic activity is simply one factor to be balanced against a peptide's potency as an antagonist.

CRF profoundly stimulates the pituitary-adrenalcortical axis, and CRF antagonists are useful to inhibit the functions of this axis in certain types of patients experiencing high ACTH and endogenous glucocorticoid production. For example, CRF antagonists may be useful in regulating pituitary-adrenal function in patients having pituitary Cushings disease or any CRF-R-bearing tumor. Preferred members of the improved CRF antagonists provided by the invention bind with high affinity to CRF receptors without significantly activating the receptors, i.e. they exhibit an intrinsic activity or agonism less than 15% of that of ovine CRF. Moreover, they are considered to have an effect when administered peripherally, e.g. i.v., s.c., intranasally, intrapulmonarily, etc., and may be used to combat stress-induced stomach disorders which result in part from acid secretion.

Most other regulatory peptides have been found to have effects upon the endocrine system, the central nervous system and upon the gastrointestinal tract. Because ACTH and β-END-LI secretion is the "sine qua non" of mammal's response to stress, it is not surprising that CRF has significant effects on the brain as a mediator of many of the body's stress responses. Accordingly, CRF antagonists delivered to the brain should also find application in modifying the mood, learning and behavior, e.g. drug addition and drug and alcohol withdrawal, of normal and mentally disordered individuals. Furthermore, CRF antagonists in the brain should ameliorate stress-induced conditions to which endogenous CRF might contribute, including some types of hypertension, anorexia nervosa, hemorrhagic stress, infertility, decreased libido, impotency and hyperglycemia. Because peripherally administered CRF antagonists reduce the levels of ACTH, β-END, β-lipotropin, other pro-opiomelanocortin gene products and corticosterone, administration of the antagonists may be used to reduce the effects of all of these substances on the brain to thereby influence memory, mood, pain appreciation, etc., and more specifically, alertness, depression and/or anxiety, as well as to modulate the immune system, gastrointestinal tract and adrenalcortical growth and function. They may also be used to treat HIV infections and Alzheimer's disease.

Because CRF antagonists will block the hypothalamic pituitary axis (HPA) and therefore block ACTH and corticosterone secretion in instances when the desired effects of administration may be on other functions (e.g. immune, neuronal, etc.), hormonal replacement therapy (i.e. administration of ACTH and/or corticosterone) may be advisable as an adjunct to CRF antagonist therapy, as necessary to maintain homeostasis. As a parallel example, testosterone replacement is often used when treating normal humans with GnRH antagonists for male contraception in order to retain libido. Such hormonal replacement is not indicated in the case of treatment of prostate cancer.

All CRF-related peptides have been shown to dilate the mesenteric vascular bed. CRF antagonists should also be of use for decreasing blood flow to the gastrointestinal tract of mammals, particularly humans. Also, because CRF influences gastric acid production, CRF antagonists should also be effective to modulate gastrointestinal functions, including abdominal bowel syndrome and inflammatory diseases.

CRF antagonists or the nontoxic addition salts thereof, combined with a pharmaceutically acceptable carrier to form a pharmaceutical composition, may be administered to mammals, including humans, either intravenously, subcutaneously, intramuscularly, intrapulmonarily, percutaneously, e.g. intranasally, intracerebroventricularly or orally. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans may be employed by a physician to inhibit endogenous glucocorticoid production or for possible uses outlined above. Administration may be in a variety of dosage forms such as tablets, lozenges, powders, syrups, injectable solutions, injectable depot formulations and the like. The required dosage will vary with the particular condition being treated, with the severity of the condition and with the duration of desired treatment, and multiple dosages may be used for a single day. In order to block the stress-related effects of endogenous CRF within the central nervous system, it may be necessary to deliver the CRF antagonists into the cerebral ventricle or spinal fluid. Alternatively, a means of modifying the antagonists so that they could penetrate the blood-brain barrier should be found. For parental administration, solutions in peanut oil, in aqueous propylene glycol, or in sterile aqueous solution may be employed; sterile aqueous media are readily available. Such aqueous solutions, which are suitably buffered, are especially suitable for intravenous (i.v.), intramuscular, subcutaneous (s.c.) and intraperitoneal administration. For s.c. administration, corn oil or a 3-6% mannitol solution may be preferred. Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, hydriodide, cinnamate, sulphate, sulfamate, sulfonate, phosphate, tannate, oxalate, fumarate, gluconate, alginate, maleate, acetate, trifluoroacetate, citrate, benzoate, succinate, pamoate, malate, ascorbate, tartrate and the like which can be prepared in a conventional manner. The salts of trifluoroacetic acid and pamoic acid may be preferred. If the active ingredient is to be administered in tablet form, the tablet may contain a binder or excipient, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

It may also be desirable to deliver the CRF antagonist peptide over prolonged periods of time, for example, for periods of one week or considerably longer, from a single administration, and slow release, depot or implant dosage forms may be utilized. For example, a suitable, slow-release depot formulation for injection may contain the CRF antagonist or a salt thereof dispersed or encapsulated in a slow degrading, non-toxic or non-antigenic polymer such as a polylactic acid/polyglycolic acid polymer, for example, as described in U.S. Pat. No. 3,773,919.

The peptides should be administered under the guidance of a physician in single or multiple doses, and pharmaceutical compositions will usually contain the peptide in conjunction with a known, pharmaceutically-acceptable carrier that may extend its duration of action. The effective dosage generally depends on the intended route of administration and other factors such as age and weight of the patient, as generally known to a physician, and also upon the illness being treated. Usually, the dosage will be from about 0.01 to about 10 milligrams of the peptide per kilogram of the body weight of the host animal. For the treatment of inflammatory diseases about 0.01 to about 1 mg/kg is generally employed; for gastrointestinal diseases about 0.01 to about 1 mg/kg, as well as for anorexia nervosa, hemorrhagic stress, treatment of drug and alcohol withdrawal symptoms and treatment of fertility problems. The daily dosage may be given in a single dose or up to three divided doses.

As mentioned hereinbefore, CRF receptors have now been cloned and are disclosed in the aforementioned Chen et al. article, in Perrin, M., et al., *P.N.A.S*, 92, 2969-2973 (March 1995), and in Lovenberg, T., et al., *P.N.A.S.*, 92, 836-840 (January 1995). Binding affinity is a term used to refer to the strength of interaction between ligand and receptor. To demonstrate binding affinity for a CRF receptor, the peptides of the invention are easily evaluated using a tracer ligand of known affinity, such as $^{125}$I-radiolabelled oCRF or [D-Tyr$^{12}$, Nle$^{21,38}$]-r/hCRF(12-41), in binding assay experiments which are well known in this art. The results of such assays indicate the affinity at which each ligand binds to a CRF receptor, expressed in terms of $K_i$, an inhibitory binding affinity constant relative to such a known standard. $K_i$ (inhibitory binding affinity constant) is determined using a "standard" or "tracer" radioactive ligand and thus measures the displacement of the tracer from the receptor or binding protein; it is most properly expressed with reference to such tracer. However, so long as these assays are carefully performed under specific conditions with relatively low concentrations of receptor or the like, the calculated $K_i$ will be substantially the same as its dissociation constant $K_D$. Dissociation constant $K_D$ is representative of the concentration of ligand necessary to occupy one-half (50%) of the binding sites of a receptor or the like. It is particularly efficient to test for $K_i$ because only a single tracer need be labelled, e.g. radioiodinated. A given ligand having a high binding affinity for a CRF receptor will require the presence of very little ligand to bind at least 50% of the available binding sites so that the $K_D$ value for that ligand and receptor will be a small number. On the other hand, a given ligand having a low binding affinity for a particular CRF receptor will require the presence of a relatively high level of the ligand to bind 50% of the sites, so that the $K_D$ value for that ligand and receptor will be a large number.

With respect to a particular receptor protein, a CRF analog peptide having a $K_D$ of about 10 nM or less means that a concentration of the ligand (i.e., the CRF analog peptide) of no greater than about 10 nM will be required to occupy at least 50% of the active binding sites of the receptor protein. Such values may be fairly determined from the results obtained using a radioiodinated standard and no more than approximately 0.8 nM of the receptor (approximately 10-20 pmol receptor/mg membrane protein). Preferred peptides provided by this invention have a binding affinity ($K_D$) such that a ligand concentration of about 10 nanomolar or less is required in order to occupy (or bind to) at least 50% of the receptor binding sites, and these are considered to have high affinity. Some of these CRF analog peptides have a binding affinity of about 2 nM or less. Generally, for purposes of this application, a dissociation constant of about 5 nanomolar or lower is considered to be an indication of strong affinity, and a $K_D$ of about 2 nanomolar or less is an indication of very strong affinity. For example, the cyclic peptide of Example I C binds CRF-RA with very strong affinity, having a $K_D$=about 2.0 nanomolar. It is also considered to be particularly advantageous that some of the CRF analog peptides have a substantially higher affinity for one of the two families of CRF-RA and CRF-RB receptors so that they are thus selective in their biological effect.

These binding assays employing CRF receptors are straightforward to perform and can be readily carried out with initially identified or synthesized peptides to determine whether such peptides will likely be effective CRF antagonists. Generally, effective CRF antagonist peptides will exhibit not more than about 25% intrinsic activity in in vitro testing, and usually not more than about 5%, e.g. will not stimulate the secretion of ACTH at a level more than about 25% of a similar molar concentration of ovine CRF(1-41). However, such a criterion is not considered critical, as experience has shown that such intrinsic agonist activity very often does not translate into in vivo effects and thus may be acceptable. Such binding assays can be carried out in a variety of ways as well known to one of skill in the art. A detailed example of such an assay is set forth in the Perrin, M., et al., *Endocrinology* article. Competitive binding assays employing the peptide of Example I C or IV A are particularly contemplated to evaluate whether candidate peptides and nonpeptides have high affinity for each of the various CRF receptors, e.g. CRF-RA, CRF-RB$_L$ and CRF-RB$_S$ as a first step in determining whether a candidate is an effective antagonist. In such assays, an appropriate cyclic CRF antagonist is appropriately labeled with a substance that is readily detected, such as a radioactive isotope, e.g. $^{125}$I, or an enzyme or some other suitable tag, such as one that fluoresces.

The use of competitive binding assays is considered particularly valuable for screening candidates for new drugs, e.g. to identify new CRF-like peptides or other compounds having even greater or more selective binding affinity for CRF receptors, which candidates would therefore be potentially useful as drugs. In the assay, one determines the ability of the candidate antagonist to displace the labelled peptide. Such screening assays as described hereinbefore may be used with a radiolabelled cyclic CRF antagonist, e.g., (cyclo 30-33) [I$^{125}$-D-Tyr$^{12}$, Nle$^{21,38}$, Glu$^{30}$, D-His$^{32}$, Lys$^{33}$]r/hCRF(12-41) to screen for potential CRF agonists. Assays employing a labelled CRF antagonist with high affinity may be used to screen for more potent antagonists of CRF. They may also be labelled with an enzyme or some other suitable tag.

As used herein all temperatures are ° C. and all ratios are by volume. Percentages of liquid materials are also by volume. By lower alkyl is meant $C_1$ to $C_6$.

Although the invention has been described with regard to its preferred embodiments, which constitute the best mode presently known to the inventor, it should be understood that various changes and modifications as would be obvious to one having the ordinary skill in this art may be made without departing from the scope of the invention which is set forth in the claims appended hereto. For example, pharmaceutically acceptable salts and other comparable formulations, although not specifically recited, are clearly equivalents of the claimed subject matter. Moreover, substitutions and modifications at other positions throughout the CRF peptide chain as indicated in the first general formula in the detailed description may be made without detracting from the potency of the antagonists. Developments in the field have shown that peptides having the various specified residues in the molecule exhibit CRF activity. The N-terminus of the 33-residue analogs can be extended by Tyr or D-Tyr and is preferably acylated by an acyl group having 20 to 15 or less carbon atoms, preferably by one having 7 or less, e.g. acetyl. When D-Tyr is included, for purposes of radioiodination, for example at the N-terminus, instead of Lys$^{28}$ it may be preferable to substitute Arg which is considered an equivalent at this position.

Instead of the simple amide at the C-terminus, a lower alkyl-substituted amide, i.e., 1-4 carbon atoms, e.g., methylamide or ethylamide, may be incorporated. An equivalent lactam bond can also be created by linking the sidechains of Lys$^{22}$ and Glu$^{25}$; however, the bonds illustrated hereinbefore are preferred. The amino group which is reacted to form the 22-25 lactam cyclizing bond may be alkylated, as by adding a methyl group; such changes are considered to create equivalent cyclic peptides. All such aforementioned peptides are considered as being within the scope of the invention.

Various features of the invention are emphasized in the claims which follow.

What is claimed is:

1. A cyclic corticotropin releasing factor (CRF) antagonist peptide, or a pharmaceutically acceptable salt thereof, which peptide has the amino acid sequence:

Y-Asp-Leu-Thr-D-Phe-His-Leu-Leu-Arg-Glu-Val-Leu-Glu-Nle-Ala-Arg-Ala-R$_{17}$-Gln-R$_{19}$-Ala-Gln-

wherein Y is an acyl group having up to 20 carbon atoms; R$_{17}$ is Glu or C$^\alpha$CH$_3$-L-leucine (CML); R$_{19}$ is 2-aminoisobutyric acid (Aib), CML, C$^\alpha$CH$_3$-L-phenylalanine (CMP), or C$^\alpha$CH$_3$-L-valine (CMV); R$_{24}$ is Aib, CML, D-CML, D-Aph (Cbm) or D-Aph(Hor); R$_{26}$ is Asn or Aib, R$_{32}$ is CMP, CMV, CML, or Aib.

2. A cyclic CRF antagonist peptide having the formula:

Ac-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg-Lys-Leu-Nle-Glu-Aib-Ile-NH$_2$.

3. A cyclic CRF antagonist peptide having the formula:

Ac-Asp-Leu-Thr-D-Phe-His-Leu-Leu-Arg-Glu-Val-Leu-Glu-Nle-Ala-Arg-Ala-Glu-Gln-CMV-Ala-Gln-Glu-Ala-Aib-Lys-Asn-Arg-Lys-Leu-Nle-Glu-CMV-Ile-NH$_2$;
or
Ac-Asp-Leu-Thr-D-Phe-His-Leu-Leu-Arg-Glu-Val-Leu-Glu-Nle-Ala-Arg-Ala-Glu-Gln-CMV-Ala-Gln-Glu-Ala-Aib-Lys-Asn-Arg-Lys-Leu-Nle-Glu-Aib-Ile-NH$_2$;
or
Ac-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg-Lys-Leu-Nle-Glu-CMV-Ile-NH$_2$.

4. A cyclic CRF antagonist peptide having the formula:

Ac-Asp-Leu-Thr-D-Phe-His-Leu-Leu-Arg-Glu-Val-Leu-Glu-Nle-Ala-Arg-Ala-Glu-Gln-CMP-Ala-Gln-Glu-Ala-Aib-Lys-Asn-Arg-Lys-Leu-Nle-Glu-CMP-Ile-NH$_2$;
or
Ac-Asp-Leu-Thr-D-Phe-His-Leu-Leu-Arg-Glu-Val-Leu-Glu-Nle-Ala-Arg-Ala-Glu-Gln-Aib-Ala-Gln-Glu-Ala-Aib-Lys-Asn-Arg-Lys-Leu-Nle-Glu-CMP-Ile-NH$_2$;
or
Ac-Asp-Leu-Thr-D-Phe-His-Leu-Leu-Arg-Glu-Val-Leu-Glu-Nle-Ala-Arg-Ala-Glu-Gln-CMP-Ala-Gln-Glu-Ala-Aib-Lys-Asn-Arg-Lys-Leu-Nle-Glu-Aib-Ile-NH$_2$;
or
Ac-Asp-Leu-Thr-D-Phe-His-Leu-Leu-Arg-Glu-Val-Leu-Glu-Nle-Ala-Arg-Ala-Glu-Gln-CMP-Ala-Gln-Glu-Ala-Aib-Lys-Asn-Arg-Lys-Leu-Nle-Glu-CML-Ile-NH$_2$.

5. A cyclic CRF antagonist peptide having the formula:

Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-D-Aph(Cbm)-Lys-Asn-Arg-Lys-Leu-Nle-Glu-CML-Ile-NH$_2$;
or
Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-CML-Lys-Asn-Arg-Lys-Leu-Nle-Glu-CML-Ile-NH$_2$;
or
Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-D-CML-Lys-Asn-Arg-Lys-Leu-Nle-Glu-CML-Ile-NH$_2$;
or
Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-D-Aph(Hor)-Lys-Asn-Arg-Lys-Leu-Nle-Glu-CML-Ile-NH$_2$.

6. The cyclic CRF antagonist peptide of claim 1 wherein the acyl group is selected from the group consisting of acetyl, propionyl, butyroyl, valeroyl, hexanoyl, octanoyl, decanoyl, tetradecanoyl, and 21-amino-4,7,10,13,16,19-hexaoxaheneicosanoyl.

7. The cyclic CRF antagonist peptide of claim 1, wherein R$_{19}$ is Aib, wherein R$_{24}$ is Aib, and R$_{32}$ is Aib.

8. The cyclic CRF antagonist peptide of claim 7 wherein the acyl group is selected from the group consisting of acetyl, propionyl, butyroyl, valeroyl, hexanoyl, octanoyl, decanoyl, tetradecanoyl, and 21-amino-4,7,10,13,16,19-hexaoxaheneicosanoyl.

9. A cyclic CRF antagonist peptide, or a pharmaceutically acceptable salt thereof, which peptide has the amino acid sequence:

Y-R$_1$-R$_2$-R$_3$-D-Phe-His-Leu-Leu-Arg-Glu-Val-Leu-Glu-Nle-Ala-Arg-Ala-Glu-Gln-Aib-R$_{20}$-R$_{21}$-Glu-R$_{23}$-Aib-R$_{25}$-R$_{26}$-Arg-Lys-Leu-Nle-R$_{31}$-Aib-Ile-NH$_2$ wherein Y is H, Tyr or D-Tyr or an acyl group having about 20 or fewer carbon atoms; $R_1$ is Asp or des-$R_1$; $R_2$ is Leu or des-$R_2$; $R_3$ is Ser or Thr or des-$R_3$; $R_{20}$ is Ala or Aib; $R_{21}$ is Gln or Aib; $R_{23}$ is Ala or Aib; $R_{25}$ is Lys or Orn; $R_{26}$ is Asn or Aib, and; $R_{31}$ is Glu.

10. The cyclic CRF antagonist peptide of claim 9 wherein the acyl group is selected from the group consisting of acetyl, propionyl, butyroyl, valeroyl, hexanoyl, octanoyl, decanoyl, tetradecanoyl, and 21-amino-4,7,10,13,16,19-hexaoxaheneicosanoyl.

11. The cyclic CRF antagonist peptide of claim 9 wherein the acyl group is acetyl.

12. The cyclic CRF antagonist peptide of claim 9 wherein the acyl group is propionyl.

13. The cyclic CRF antagonist peptide of claim 9 wherein the acyl group is butyroyl.

14. The cyclic CRF antagonist peptide of claim 9 wherein the acyl group is valeroyl.

15. The cyclic CRF antagonist peptide of claim 9 wherein the acyl group is hexanoyl.

16. The cyclic CRF antagonist peptide of claim 9 wherein the acyl group is octanoyl.

17. The cyclic CRF antagonist peptide of claim 9 wherein the acyl group is decanoyl.

18. The cyclic CRF antagonist peptide of claim 9 wherein the acyl group is tetradecanoyl.

19. The cyclic CRF antagonist peptide of claim 9 wherein the acyl group is 21-amino-4,7,10,13,16,19-hexaoxaheneicosanoyl.

20. The cyclic CRF antagonist peptide of claim 1, wherein Y is an acyl group having up to 12 carbon atoms.

21. The cyclic CRF antagonist peptide of claim 1, wherein Y is an acyl group having up to 15 carbon atoms.

22. The cyclic CRF antagonist peptide of claim 1, wherein Y is an acyl group and the carbon atoms are selected from the group consisting of Ac, For, Acr and Bz.

23. A pharmaceutical composition comprising the cyclic CRF antagonist peptide of claim 1 and a pharmaceutically acceptable carrier.

24. A cyclic CRF antagonist peptide having the formula:

Ac-Asp-Leu-Thr-D-Phe-His-Leu-Leu-Arg-Glu-Val-
Leu-Glu-Nle-Ala-Arg-Ala-Glu-Gln-Aib-Ala-Gln-
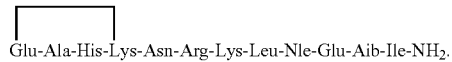
Glu-Ala-His-Lys-Asn-Arg-Lys-Leu-Nle-Glu-Aib-Ile-NH$_2$.

25. A cyclic CRF antagonist peptide having the formula:

Ac-Asp-Leu-Thr-D-Phe-His-Leu-Leu-Arg-Glu-Val-
Leu-Glu-Nle-Ala-Arg-Ala-Glu-Gln-CML-Ala-Gln-
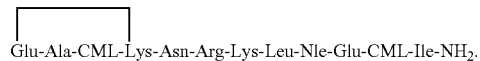
Glu-Ala-CML-Lys-Asn-Arg-Lys-Leu-Nle-Glu-CML-Ile-NH$_2$.

26. A cyclic CRF antagonist peptide having the formula:

Ac-Asp-Leu-Thr-D-Phe-His-Leu-Leu-Arg-Glu-Val-
Leu-Glu-Nle-Ala-Arg-Ala-Glu-Gln-CML-Ala-Gln-
Glu-Ala-D-Aph(Cbm)-Lys-Asn-Arg-Lys-Leu-Nle-Glu-CML-Ile-NH$_2$.

27. A cyclic CRF antagonist peptide having the formula:

Ac-Asp-Leu-Thr-D-Phe-His-Leu-Leu-Arg-Glu-Val-
Leu-Glu-Nle-Ala-Arg-Ala-Glu-Gln-CML-Ala-Gln-
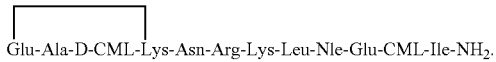
Glu-Ala-D-CML-Lys-Asn-Arg-Lys-Leu-Nle-Glu-CML-Ile-NH$_2$.

* * * * *